US009700050B2

(12) United States Patent
Ikeda

(10) Patent No.: US 9,700,050 B2
(45) Date of Patent: Jul. 11, 2017

(54) METHOD OF CONTROLLING PESTS

(71) Applicant: SUMITOMO CHEMICAL COMPANY, LIMITED, Tokyo (JP)

(72) Inventor: Hajime Ikeda, Kasai (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 63 days.

(21) Appl. No.: 14/099,308

(22) Filed: Dec. 6, 2013

(65) Prior Publication Data

US 2015/0157017 A1 Jun. 11, 2015

(51) Int. Cl.
*A01N 43/84* (2006.01)

(52) U.S. Cl.
CPC .................................... *A01N 43/84* (2013.01)

(58) Field of Classification Search
None
See application file for complete search history.

(56) References Cited

U.S. PATENT DOCUMENTS 3,799,758 A 3/1974 Franz
2010/0317523 A1* 12/2010 Ikeda .................... A01N 43/78
504/223

FOREIGN PATENT DOCUMENTS

WO WO 2013/122241 A1 8/2013

OTHER PUBLICATIONS

Meister et al., "The Building Blocks for Global Food Security", MeisterPro Crop Protection Handbook 2012, vol. 98, pp. 6-7, 442-443, ISBN: 1-892829-25-8.

* cited by examiner

*Primary Examiner* — Tracy Vivlemore
*Assistant Examiner* — Monica Shin
(74) *Attorney, Agent, or Firm* — Birch, Stewart, Kolasch & Birch, LLP

(57) ABSTRACT

The present invention relates to a method of controlling weeds in a crop field, the method including treating the crop field with crystal of flumioxazin described in the specification, before sowing or planting, at the same time of sowing or planting, or after sowing or planting crop seeds or vegetative organs such as tubers, bulbs, or stem fragments which are treated with one or more compounds selected from the following group B; Group B: neonicotinoid type compounds, diamide type compounds, carbamate type compounds, organic phosphorous type compounds, biological nematicidal compounds, other insecticidal compounds and nematicidal compounds, azole type compounds, strobilurin type compounds, metalaxyl type compounds, SDHI compounds, and other fungicidal compounds and plant growth regulators. According to the method of controlling pests of the present invention, weeds in clop fields can be efficiently controlled.

2 Claims, No Drawings

METHOD OF CONTROLLING PESTS

BACKGROUND OF THE INVENTION

Field of the Invention

The present invention relates to a pest control method, that is, a method of controlling pests such as harmful arthropod pests, nematodes, plant pathogens, and/or weeds.

Description of the Related Art

Various compounds are known as effective components for insecticides, nematicides, or fungicides. Also, flumioxazin is known as an effective component for herbicides.

PRIOR ART LITERATURE

Patent Literature

Patent Literature 1: U.S. Pat. No. 3,799,758

Non-Patent Literatures

Non-Patent Literature 1: Crop Protection Handbook, vol. 98 (2012) Meister Publishing Company, ISBN: 1-892829-25-8)

Non-Patent Literature 2: Compendium of Pesticide Common Names (http://www.alanwood.net/pesticides/)

SUMMARY OF THE INVENTION

It is an object of the present invention to provide a method for producing an excellent effect on pest control in crop fields.

The present invention relates to a method of controlling pests grown in a crop field by treating the crop field with flumioxazin constituted of a specific crystal structure before sowing or planting, at the same time of sowing or planting, or after sowing or planting crop seeds or vegetative organs such as tubers, bulbs, or stem fragments which are treated with one or more specific insecticidal compounds, nematicidal compounds, or fungicidal compounds.

The present invention is as follows.

[1] A method of controlling weeds in a crop field, the method including treating the crop field with crystal of flumioxazin, before sowing or planting, at the same time of sowing or planting, or after sowing or planting crop seeds or vegetative organs such as tubers, bulbs, or stem fragments which are treated with one or more compounds selected from the following group B;

Group B: neonicotinoid type compounds, diamide type compounds, carbamate type compounds, organic phosphorous type compounds, biological nematicidal compounds, other insecticidal compounds and nematicidal compounds, azole type compounds, strobilurin type compounds, metalaxyl type compounds, SDHI compounds, and other fungicidal compounds and plant growth regulators, wherein the crystal of flumioxazin shows a powder X-Ray diffraction pattern having diffraction peaks with 2θ values (°) shown in Table, said pattern being obtained by CuKα rays diffraction analysis, Table

| 2θ value (°) |
|---|
| 9.8 ± 0.1 |
| 11.4 ± 0.1 |
| 12.7 ± 0.1 |
| 13.8 ± 0.1 |
| 16.0 ± 0.1 |
| 16.4 ± 0.1 |
| 16.7 ± 0.1 |

[2] A method of controlling pests in a crop field, the method including the steps of:

treating crop seeds or vegetative organs such as tubers, bulbs, or stem fragments with one or more compounds selected from the group B: neonicotinoid type compounds, diamide type compounds, carbamate type compounds, organic phosphorous type compounds, biological nematicidal compounds, other insecticidal compounds and nematicidal compounds, azole type compounds, strobilurin type compounds, metalaxyl type compounds, SDHI compounds, and other fungicidal compounds and plant growth regulators; and treating the crop field with crystal of flumioxazin, before sowing or planting, at the same time of sowing or planting, or after sowing or planting the crop seeds or vegetative organs such as tubers, bulbs, or stem fragments which are treated with the compounds of the group B, wherein the crystal of flumioxazin shows a powder X-Ray diffraction pattern having diffraction peaks with 2θ values (°) shown in Table, said pattern being obtained by CuKα rays diffraction analysis, Table

| 2θ value (°) |
|---|
| 9.8 ± 0.1 |
| 11.4 ± 0.1 |
| 12.7 ± 0.1 |
| 13.8 ± 0.1 |
| 16.0 ± 0.1 |
| 16.4 ± 0.1 |
| 16.7 ± 0.1 |

[3] The control method according to [1] or [2], wherein the group B is the following compounds:

group B:

B-1. neonicotinoid type compounds: clothianidin, thiamethoxam, imidacloprid, dinotefuran, nitenpyram, acetamiprid, and thiacloprid;

diamide type compounds: flubendiamide, chlorantraniliprole, cyantraniliprole, and compounds represented by the formula (I):

(I)

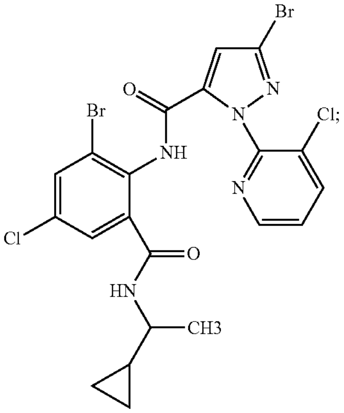

B-2. carbamate type compounds: aldicarb, oxamyl, thiodicarb, carbofuran, carbosulfan, and dimethoate;

B-3. organic phosphorous type compounds: fenamiphos, imicyafos, fensulfothion, terbufos, fosthiazate, phosphocarb, dichlofenthion, isamidofos, isazophos, ethoprophos, cadusafos, chlorpyrifos, heterofos, mecarphon, phorate, thionazin, triazophos, diamidafos, fosthietan, and phosphamidon;

B-4. biological nematicidal compounds: Harpin Protein, *Pasteuria nishizawae, Pasteuria penetrans, Myrothecium verrucaria, Burholderia cepacia, Bacillus chitonosporus, Paecilomyces lilacinus, Bacillus amyloliquefaciens, Bacillus firmus, Bacillus subtillis, Bacillus pumulis, Trichoderma harzianum, Hirsutellarhossiliensis, Hirsutellaminnesotensis, Verticillium chlamydosporum*, and *Arthrobotrys dactyloides;*

B-5. other insecticidal compounds and nematicidal compounds: fipronil, ethiprole, sulfoxaflor, flupyradifurone, beta-cyfluthrin, tefluthrin, chlorpyrifos, abamectin, spirotetramat, and fluensulfone;

B-6. azole type compounds: azaconazole, bitertanol, bromuconazole, cyproconazole, diphenoconazole, diniconazole, epoxyconazole, fenbuconazole, fluquinconazole, flusilazole, flutriafol, hexaconazole, imibenconazole, ipconazole, metconazole, mycrobutanil, penconazole, propiconazole, prothioconazole, simeconazole, tebuconazole, tetraconazole, triadimenol, triticonazole, fenarimol, nuarimol, pyrifenox, imazalil, oxpoconazole-fumarate, pefurazoate, prochloraz, and triflumizol;

B-7. strobilurin type compounds: kresoxim-methyl, azoxystrobin, trifloxystrobin, fluoxastrobin, picoxystrobin, pyraclostrobin, dimoxystrobin, pyribencarb, metominostrobin, orysastrobin, and N-methyl-2-[2-(2,5-dimethylphenoxyl) methyl]phenyl-2-methoxyacetamide (racemic or enantiomer, containing a mixture of R-enantiomer and S-enantiomer (optional ratio));

B-8. metalaxyl type compounds: metalaxyl and metalaxyl-M;

B-9. SDHI compounds: sedaxane, penflufen, carboxin, boscalid, furametpyr, flutolanil, fluxapyroxad, isopyrazam, fluopyram, and thifluzamide;

B-10. other fungicidal compounds: tolclophos-methyl, thiram, Captan, carbendazim, thiophanate-methyl, mancozeb, thiabendazole, isotianil, triazoxide, (RS)-2-methoxy-N-methyl-2-[α-(2,5-xylyloxy)-o-tolyl]acetamide, fludioxonil, ethaboxam, 3-chloro-5-phenyl-6-methyl-4-(2,6-difluorophenyl)pyridazine, 3-cyano-5-phenyl-6-methyl-4-(2,6-difluorophenyl)pyridazine, and N-(1,1,3-trimethylindan-4-yl)-1-methyl-3-difluoromethylpyrazole-4-carboxylic acid amide (racemic or enantiomer, containing a mixture of R-enantiomer and S-enantiomer (optional ratio)); and B-11. plant growth inhibitors: ethephon, chlormequat-chloride, mepiquat-chloride, and 4-oxo-4-(2-phenylethyl) aminobutyric acid.

[4] The control method according to anyone of [1] to [3], wherein the crop is soybean, peanut, common bean, pea, corn, cotton, wheat, rice, sunflower, potato, sugar cane, or vegetables.

[5] The control method according to anyone of [2] to [4], wherein the pests are weeds and/or arthropods and/or plant pathogens.

[6] The control method according to any one of [2] to [4], wherein the pests are weeds.

Pests in crop fields can be controlled by the method of controlling pests according to the present invention.

DETAILED DESCRIPTION OF THE PREFERRED EMBODIMENTS

A method of controlling pests according to the present invention (hereinafter referred to as a method of the present invention) includes the steps of:

(1) treating crop seeds or vegetative organs such as tubers, bulbs, or stem fragments with one or more compounds selected from the group B consisting of specific insecticidal compounds, nematicidal compounds, and fungicidal compounds; and (2) treating a crop field with crystal of flumioxazin, before sowing or planting, at the same time of sowing or planting, or after sowing or planting the crop seeds or vegetative organs such as tubers, bulbs, or stem fragments which are treated with the compounds of the group B, wherein the crystal of flumioxazin shows a powder X-Ray diffraction pattern having diffraction peaks with 2θ values (°) shown in Table, said pattern being obtained by CuKα rays diffraction analysis, Table

| 2θ value (°) |
|---|
| 9.8 ± 0.1 |
| 11.4 ± 0.1 |
| 12.7 ± 0.1 |
| 13.8 ± 0.1 |
| 16.0 ± 0.1 |
| 16.4 ± 0.1 |
| 16.7 ± 0.1 |

Hereinafter, the crystal of flumioxazin is referred to as "A-type crystal flumioxazin".

Examples of the crops to which the method of the present invention is applied include food crops such as soybean, corn, cotton, wheat, barley, rye, triticale, rice, peanut, common bean, lima bean, azuki bean, cowpeas, mung bean, black lentil, scarlet runner bean, vigna umbellate, moth bean, tepary bean, broad bean, pea, garbanzo bean, lentil, lupine, pigeon pea, and potato; forage crops such as sorghum, oat, and alfalfa; industrial crops such as sugar beet, sunflower, rapeseed, and sugar cane; and garden crops such as Solanaceae vegetables (for example, eggplant, tomato, greenpepper, bell pepper, and hot pepper), Cucurbitaceae vegetables (for example, cucumber, pumpkin, zucchini, watermelon, and melon), Cruciferous vegetables (for example, Japanese radish, turnip, horseradish, kohlrabi, Chinese cabbage, cabbage, brown mustard, broccoli, and cauliflower), Compositae vegetables (for example, burdock, garland chrysanthemum, artichoke, and lettuce), Liliaceae vegetables (for example, Welsh onion, onion, garlic, asparagus), Umbelliferae vegetables (carrot, parsley, celery, and parsnip), Chenopodiaceae vegetables (for example, spinach and Swiss chard), Labiatae vegetables (for example, Japanese mint, mint, basil, and lavender), strawberry, sweet potato, yam, and aroid.

The method of the present invention is applied particularly to soybean, peanut, common bean, pea, corn, cotton, wheat, rice, sunflower, potato, sugar cane, or vegetables.

When the method of the present invention is applied to sugar cane, stem fragments cut so as to have one stalk may be used as the stem fragment of sugar cane, or stem fragments having a size of 2 cm to 15 cm may be used in the cultivation of sugar cane. Sugarcane cultivation methods using such stem fragments are publicly known (WO 09/0000398, WO 09/000399, WO 09/000400, WO 09/000401, and WO 09/000402) and performed under the brand name of Plene (trademark).

The above crops include plants to which resistance to Protoporphyrinogen IX oxidase inhibitors such as flumioxazin; 4-hydroxyphenylpyrubic acid dioxygenase inhibitors such as isoxaflutole; acetolactic acid synthase inhibitors such as imazethapyr and thifensulfuron-methyl; 5-enolpyruvylshikimate-3-phosphoric acid synthase inhibitors such as glyphosate; glutamine synthetase inhibitors such as glufosinate; auxin type herbicides such as 2,4-D and dicamba; and herbicides such as bromoxinyl are imparted by classical breeding methods or genetic modification technologies.

As examples of crops to which resistance has been imparted by classical breeding methods, corn resistant to imidazolinone type acetolactic acid synthase inhibitory herbicides such as imazethapyr is given and has already been commercially available under the trade name of Clearfield (trademark). Examples of such crops include STS soybeans resistant to sulfonylurea type acetolactic acid synthase inhibitory herbicides such as thifensulfuron-methyl. Similarly, examples of a plant to which resistance to an acetyl CoA carboxylase inhibitor such as trione oxime-based or aryloxyphenoxypropionic acid-based herbicide has been imparted by classical breeding methods include SR corn.

Examples of a plant to which resistance has been imparted by genetic modification technologies include corn, soybeans and cotton resistant to glyphosate, and they have already been commercially available under the trade names of RoundupReady (registered trade mark), Agrisure (registered trademark) GT, Gly-Tol (registered trademark) and the like. Similarly, there are corn, soybeans and cotton resistant to glufosinate by genetic modification technologies, and they have already been commercially available under the trade names of LibertyLink (registered trademark) and the like. There are varieties of corn and soybeans under the trade names of Optimum (registered trademark) GAT (registered trade mark), which are resistant to both of glyphosate and acetolactic acid synthase inhibitor. Similarly, there are soybeans resistant to imidazolinone type acetolactic acid synthase inhibitors by genetic modification technologies, and they have been developed under the name of Cultivance. Similarly, there is cotton resistant to bromoxynil by genetic modification technologies, and this has already been commercially available under the trade name of BXN (registered trademark). Similarly, there is a variety of soybean sold under the trade name of RoundupReady (registered trademark) 2 Xtend as a soybean resistant to both of glyphosate and dicamba by genetic modification technologies. Similarly, there has been developed cotton resistant to both of glyphosate and dicamba by genetic modification technologies.

A gene encoding aryloxyalkanoate dioxygenase may be introduced to produce a crop which becomes resistant to phenoxy acid type herbicides such as 2,4-D, MCPA, dichlorprop and mecoprop, and aryloxyphenoxypropionic acid type herbicides such as quizalofop, haloxyfop, fluazifop, diclofop, fenoxaprop, metamifop, cyhalofop and clodinafop (Wright et al. 2010: Proceedings of National Academy of Science. 107 (47): 20240-20245). Cultivars of soybean and cotton, which show the resistance to 2,4-D, have been developed under the brand of Enlist.

A gene encoding a 4-hydroxyphenyl pyruvic acid dioxygenase (hereinafter referred to as HPPD) inhibitor, the gene having resistance to HPPD, may be introduced to create a plant resistant to a HPPD inhibitor (US2004/0058427). A gene capable of synthesizing homogentisic acid which is a product of HPPD in a separate metabolic pathway even if HPPD is inhibited by a HPPD inhibitor is introduced, with the result that a plant having resistance to the HPPD inhibitor can be created (WO02/036787). A gene expressing excess HPPD may be introduced to produce HPPD in such an amount as not to adversely affect the growth of plants even in the presence of a HPPD inhibitor, with the result that a plant having resistance to the HPPD inhibitor can be created (WO96/38567). Besides introduction of the gene expressing excess HPPD, a gene encoding prephenate dehydrogenase is introduced in order to increase the yield of p-hydroxyphenyl pyruvic acid which is a substrate of HPPD to create a plant having resistance to the HPPD inhibitor (Rippert P et. al., 2004 Engineering plant shikimate pathway for production of tocotrienol and improving herbicide resistance. Plant Physiol. 134: 92-100).

Examples of a method of producing crops resistant to herbicides include, other than the above, the gene introducing methods described in WO98/20144, WO2002/46387, and US2005/0246800.

The above crops include, for example, crops which can synthesize selective toxins and the like known as the genus *Bacillus* by using genetic modification technologies.

Examples of the toxins developed in such genetically modified plants include insecticidal proteins derived from *Bacillus cereus* and *Bacillus popilliae*; δ-endotoxins such as Cry1Ab, Cry1Ac, Cry1F, Cry1Fa2, Cry2Ab, Cry3A, Cry3Bb1, Cry9C, Cry34, and Cry35ab derived from *Bacillus thuringiensis*; insecticidal proteins such as VIP1, VIP2, VIP3, and VIP3A; insecticidal proteins derived from nematodes; toxins produced by animals such as scorpion toxins, spider toxins, bee toxins, and neurotoxins specific to insects; filamentous fungus toxins; plant lectins; agglutinin; trypsin inhibitors, serine protease inhibitors, and protease inhibitors such as patatin, cystatin, and papain inhibitors; ribosome inactivating proteins (RIP) such as lysine, corn-RIP, abrin, lufin, saporin, and bryodin; steroid metabolic enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel and calcium channel inhibitors; juvenile hormone esterase; diuretic hormone receptors; stilbene synthase; bibenzyl synthase; chitinase; and glucanase.

The toxins expressed in these transgenic plants include hybrid toxins, partially deficient toxins and modified toxins, which derive from δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and insecticidal proteins such as VIP1, VIP2, VIP3 and VIP3A. The hybrid toxins are created by new combinations of domains having different proteins by using genetic modification technologies. As the partially defective toxins, Cry1Ab in which part of the amino acid sequences is missing is known. In the modified toxin, one or more of amino acids of a natural type toxin is replaced. Examples of these toxins and genetically modified plants capable of synthesizing these toxins are described in, for example, EP-A-0374753, WO 93/07278, WO 95/34656, EP-A-0427529, EP-A-451878, and WO 03/052073. Resistance to noxious insects belonging to order Coleoptera, order Diptera, and order Lepidoptera is imparted to plants by toxins contained in these genetically modified plants.

Also, genetically modified plants which contain one or more insecticidal genes resistant to harmful insects and develop one or more toxins have been already known and some of these plants have been put on the market. Examples of these genetically modified plants include YieldGard (registered trademark) (corn variety expressing Cry1Ab toxin), YieldGard Rootworm (registered trademark) (corn variety expressing Cry3Bb1 toxin), YieldGard Plus (registered trademark) (corn variety expressing Cry1Ab and Cry3Bb1 toxins), Herculex I (registered trademark) (corn variety expressing phosphinothricin N-acetyltransferase (PAT) for imparting resistance to a Cry1Fa2 toxin and glufosinate), NatureGard (registered trademark), AGRISURE (registered trademark) CBAdvantage (Bt11 cornborer (CB) trait), Protecta (registered trademark); and the like.

Also, genetically modified cotton which contains one or more insecticidal genes resistant to harmful insects and develops one or more toxins has been already known and some of cotton have been put on the market. Examples of these genetically modified cotton include BollGard (registered trademark) (cotton variety expressing Cry1Ac toxin), BollGard (registered trademark) II (cotton variety expressing Cry1Ac and Cry2Ab toxins), BollGard (registered trademark) III (cotton variety expressing Cry1Ac, Cry2Ab and VIP3A toxins), VipCot (registered trademark) (cotton variety expressing VIP3A and Cry1Ab toxins), WideStrike (registered trademark) (cotton variety expressing Cry1Ac and Cry1F toxins) and the like.

Examples of the plant used in the present invention also include plants such as soybeans into which a Ragl (Resistance Aphid Gene 1) gene is introduced to impart resistance to an aphid.

The plants to be used in the present invention include those provided with resistance to nematodes by using a classical breeding method or genetic modification technologies. Examples of the genetic modification technologies used to provide the resistance to nematodes include RNAi.

The above crops include those to which the ability to produce antipathogenic substances having a selective effect is imparted using genetic modification technologies. For example, PR proteins are known as an example of the antipathogenic substance (PRPs, EP-A-0392225). Such antipathogenic substances and genetically modified plants producing these antipathogenic substances are described in, for example, EP-A-0392225, WO 95/33818, and EP-A-0353191. Examples of the antipathogenic substances developed in such genetically modified plants include ion channel inhibitors such as a sodium channel inhibitor and calcium channel inhibitor (KP1, KP4, and KP6 toxins produced by virus are known); stilbene synthase; bibenzyl synthase; chitinase; glucanase; PR protein; antipathogenic substances produced by microorganisms such as peptide antibiotics, antibiotics having a heteroring, and a protein factor (referred to as a plant disease resistant gene and described in WO 03/000906) relating to plant disease resistance.

The above crops include plants to which useful traits such as an oil component reformation and amino acid-content reinforcing trait are given by genetic modification technologies. Examples of these plants include VISTIVE (trademark) (low linolenic soybean having a reduced linolenic content), high-lysine (high oil) corn (corn having an increased lysine or oil content) and the like.

Moreover, the above crops include stuck varieties obtained by combining two or more useful traits such as the above classical herbicide trait or herbicide resistant gene, gene resistant to insecticidal noxious insects, antipathogenic substance-producing gene, oil component reformation, amino acid-content reinforcing trait, and allergen reduction trait.

In the method of the present invention, examples of the compounds of the group B including specific insecticidal compounds, nematicidal compounds, fungicidal compounds, or plant growth regulators used to treat crop seeds or vegetative organs such as tubers, bulbs, or stem fragments include neonicotinoid type compounds, diamide type compounds, carbamate type compounds, organic phosphorous type compounds, biological nematicidal compounds, other insecticidal compounds and nematicidal compounds, azole type compounds, strobilurin type compounds, metalaxyl type compounds, SDHI compounds, and other fungicidal compounds and plant growth regulators.

Examples of the neonicotinoid type compounds in the present invention include the followings:

clothianidin, imidacloprid, nitenpyram, acetamiprid, thiamethoxam, thiacloprid, and dinotefuran.

Examples of the diamide type compounds in the present invention include the followings:

flubendiamide, chlorantraniliprole, cyantraniliprole, and compounds represented by the formula (I):

(I)

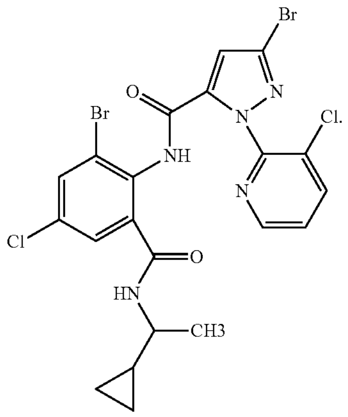

Examples of the carbamate type compounds in the present invention include the followings:

aldicarb, oxamyl, thiodicarb, carbofuran, carbosulfan, and dimethoate.

Examples of the organic phosphorous type compounds in the present invention include the followings:

fenamiphos, imicyafos, fensulfothion, terbufos, fosthiazate, phosphocarb, dichlofenthion, isamidofos, isazophos, ethoprophos, cadusafos, chlorpyrifos, heterofos, mecarphon, phorate, thionazin, triazophos, diamidafos, fosthietan, and phosphamidon.

Examples of the biological nematicidal compounds in the present invention include the followings:

Harpin Protein, *Pasteuria nishizawae, Pasteuria penetrans, Pasteuria usage, Myrothecium verrucaria, Burholderia cepacia, Bacillus chitonosporus, Paecilomyces lilacinus, Bacillus amyloliquefaciens, Bacillus firmus, Bacillus subtillis, Bacillus pumulis, Trichoderma harzianum, Hirsutella rhossiliensis, Hirsutella minnesotensis, Verticillium chlamydosporum*, and *Arthrobotrys dactyloides.*

Examples of the other insecticidal compounds and nematicidal compounds in the present invention include the followings:

fipronil, ethiprole, flupyradifurone, sulfoxaflor, beta-cyfluthrin, tefluthrin, chlorpyrifos, abamectin, spirotetramat, and fluensulfone.

Examples of the azole type compounds in the present invention include the followings:

azaconazole, bitertanol, bromuconazole, cyproconazole, difenoconazole, diniconazole, epoxyconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimenol, triticonazole, fenarimol, nuarimol, pyrifenox, imazalil, oxpoconazole fumarate, pefurazoate, prochloraz, and triflumizol.

Examples of the strobilurin type compounds in the present invention include the followings:

kresoxim-methyl, azoxystrobin, trifloxystrobin, fluoxastrobin, picoxystrobin, pyraclostrobin, dimoxystrobin, pyribencarb, metominostrobin, orysastrobin, and N-methyl-2-[2-(2,5-dimethylphenoxyl)methyl]phenyl-2-methoxyacetamide (racemic or enantiomer, containing a mixture of R-enantiomer and S-enantiomer (optional ratio), hereinafter referred to as a compound 1).

Examples of the metalaxyl type compounds include the followings:

metalaxyl and metalaxyl-M and mefenoxam.

Examples of the SDHI compounds in the present invention include the followings:

sedaxane, penflufen, carboxin, boscalid, furametpyr, flutolanil, fluxapyroxad, isopyrazam, fluopyram, and thifluzamide.

Examples of the other fungicidal compounds in the present invention include the followings:

tolclophos-methyl, thiram, Captan, carbendazim, thiophanate-methyl, mancozeb, thiabendazole, isotianil, triazoxide, (RS)-2-methoxy-N-methyl-2-[α-(2,5-xylyloxy)-o-tolyl]acetamide, fludioxonil, ethaboxam, 3-chloro-5-phenyl-6-methyl-4-(2,6-difluorophenyl)pyridazine (hereinafter referred to as a compound 2), 3-cyano-5-phenyl-6-methyl-4-(2,6-difluorophenyl)pyridazine (hereinafter referred to as a compound 3), and N-(1,1,3-trimethylindan-4-yl)-1-methyl-3-difluoromethylpyrazole-4-carboxylic acid amide (racemic or enantiomer, containing a mixture of R-enantiomer and S-enantiomer (optional ratio), hereinafter referred to as a compound 4).

Examples of the plant growth regulators in the present invention include the followings:

ethephon, chlormequat-chloride, mepiquat-chloride, and 4-oxo-4-(2-phenylethyl)aminobutyric acid (hereinafter referred to as a compound 5).

In the present invention, the compounds of the group B used to treat crop seeds, or vegetative organs such as tubers, bulbs, or stem fragments are publicly known compounds, and may be synthesized based on well known patent documents. Also, commercially available preparations or standard products may be purchased and used as the compounds of the group B.

In the step of treating crop seeds or vegetative organs such as tubers, bulbs, or stem fragments with the compounds of the group B in the present invention, the compounds of the group B are usually mixed with a carrier such as a solid carrier or liquid carrier and further added with auxiliaries for preparations such as surfactants according to the need to be formulated into preparations. The dosage is preferably an aqueous suspension preparation.

As the compounds of the group B used to treat crop seeds or vegetative organs such as tubers, bulbs, or stem fragments in the present invention, a preparation constituted of a single component may be used, two or more preparations each constituted of a single component may be used in combination, or a preparation constituted of two or more components may be used.

The compounds of the group B used for the above treatment are applied in an amount of usually 0.2 to 5000 g, and preferably 0.5 to 1000 g based on 100 kg of the crop seeds or vegetative organs such as tubers, bulbs, or stem fragments. Examples of a method for applying effective components to the crop seeds or vegetative organs such as tubers, bulbs, or stem fragments include a method in which the crop seeds or vegetative organs such as tubers, bulbs, or stem fragments are powder-coated with a preparation containing effective components; a method in which the crop seeds or vegetative organs such as tubers, bulbs, or stem fragments are dipped in a preparation containing effective components; a method in which a preparation containing effective components is sprayed on the crop seeds or vegetative organs such as tubers, bulbs, or stem fragments; and a method in which the crop seeds or vegetative organs such as tubers, bulbs, or stem fragments are coated with a carrier containing effective components.

The present invention includes the step of treating a crop field with A-type crystal flumioxazin before sowing or planting, at the same time of sowing or planting, or after sowing or planting the crop seeds or vegetative organs such as tubers, bulbs, or stem fragments which are treated with the compounds of the group B.

The A-type crystal flumioxazin used in the method of the present invention may be prepared by the methods described in Examples and modified methods thereof. A flumioxazin solution or suspension may be used as a starting material to produce the A-type crystal flumioxazin. Also, a solution or suspension of a synthetic reaction crude product containing flumioxazin may be used. A seed crystal may be added in the crystallization and in this case, it is preferable to use a crystal with the crystal form to be prepared. The amount of the seed crystals to be added is preferably 0.0005 parts by weight to 0.02 parts by weight, and more preferably 0.001 parts by weight to 0.01 parts by weight based on 1 part by weight of flumioxazin.

The A-type crystal flumioxazin may be isolated, for example, by filtration, centrifugation, or gradient method. This A-type crystal flumioxazin may be washed with a proper solvent according to the need. Also, the obtained A-type crystal flumioxazin can be improved in purity and quality by recrystallization or slurry purification. Crystals of a solvate may be converted into crystals of a non-solvate by drying with heating under reduced pressure. The degree of dryness of the crystal may be determined by analytical means such as gas chromatography. Also, the polymorph form purity of the crystal may be determined by subjecting the crystal to powder X-ray diffraction measurement to analyze the presence or absence and height of a diffraction peak specific to the solvate crystal. The A-type crystal flumioxazin is a solvate or non-solvate. When a specific hydrophilic organic solvent is used as a solvent for crystallization, there is the case where the A-type crystal flumioxazin forms a solvate. Anon-solvate is obtained by drying the solvate with heating under reduced pressure.

In the step of treating a field with the A-type crystal flumioxazin, the A-type crystal flumioxazin is usually mixed with a carrier such as a solid carrier or liquid carrier and further added with auxiliaries for preparations such as surfactants according to the need to be formulated into preparations.

Examples of a method for applying the A-type crystal flumioxazin to a field include a method in which the A-type crystal flumioxazin is sprayed on field soil and a method in which the A-type crystal flumioxazin is sprayed on weeds after the weeds are grown.

The amount of the A-type crystal flumioxazin used in the step of applying the A-type crystal flumioxazin to a field is usually 5 to 5000 g, preferably 10 to 1000 g, and more preferably 20 to 500 g per 10000 $m^2$. In this case, adjuvants may be added to the A-type crystal flumioxazin to apply the A-type crystal flumioxazin to the field.

In the present invention, the crop seeds or vegetative organs such as tubers, bulbs, or stem fragments treated with the compounds of the group B are sowed or planted in a field by a usual method. In the method of controlling pests according to the present invention, a crop field may be treated with the A-type crystal flumioxazin before sowing or planting, at the same time of sowing or planting, or after sowing or planting the crop seeds or vegetative organs such as tubers, bulbs, or stem fragments.

When a crop field is treated with the A-type crystal flumioxazin before sowing or planting the crop seeds or vegetative organs such as tubers, bulbs, or stem fragments, the A-type crystal flumioxazin is applied before 50 days to immediately before sowing or planting, preferably before 30 days to immediately before sowing or planting, more preferably before 20 days to immediately before sowing or planting, and even more preferably before 10 days to immediately before sowing or planting.

When a crop field is treated with the A-type crystal flumioxazin after sowing or planting the crop seeds or vegetative organs such as tubers, bulbs, or stem fragments, the A-type crystal flumioxazin is applied immediately after to 50 days after sowing or planting.

The method of controlling pests according to the present invention ensures that harmful arthropods, noxious nematodes and/or plant pathogens, and pests such as weeds in crop fields can be controlled.

As harmful arthropods, the following examples are given.

Noxious insects belonging to order Hemiptera: Delphacidae such as *Laodelphax striatellus, Nilaparvata lugens*, and *Sogatella furcifera*, Deltocephalidae such as *Nephotettix cincticeps* and *Nephotettix virescens*, Aphididae such as *Aphis gossypii, Myzus persicae, Brevicoryne brassicae, Macrosiphum euphorbiae, Aulacorthum solani, Rhopalosiphum padi*, and *Toxoptera citricidus*, Pentatomidae such as *Nezara antennata, Riptortus clavetus, Leptocorisa chinensis, Eysarcoris parvus, Halyomorpha mista*, and *Lygus lineolaris*, Aleyrodidae such as *Trialeurodes vaporariorum, Bemisia tabaci*, and *Bemisia argentifolii*, Coccidae such as *Aonidiella aurantii, Comstockaspis perniciosa, Unaspis citri, Ceroplastes rubens*, and *Icerya* purchase, Tingidae, and Psyllidae;

noxious insects belonging to order Lepidoptera: Pyralidae such as *Chilo suppressalis, Tryporyza incertulas, Cnaphalocrocis medinalis, Notarcha derogate, Plodia interpunctella, Ostrinia furnacalis, Ostrinia nubilaris, Hellula undalis*, and *Pediasia teterrellus*, Noctuidae such as *Spodoptera litura, Spodoptera exigua, Pseudaletia separate, Mamestra brassicae, Agrotis ipsilon, Plusia nigrisigna, Trichoplusia* spp., *Heliothis* spp., and *Helicoverpa* spp., Pieridae such as *Pieris rapae*, Tortricidae such as *Adoxophyes* spp., *Grapholita molesta, Leguminivora glycinivorella, Matsumuraeses azukivora, Adoxophyes orana fasciata, Adoxophyes* sp., *Homona magnanima, Archips fuscocupreanus*, and *Cydia pomonella*, Gracillariidae such as *Caloptilia theivora* and *Phyllonorycter ringoneella*, Carposinidae such as *Carposina niponensis*, Lyonetiidae such as *Lyonetia* spp., *Lymantriidae* such as *Lymantriidae* spp. and *Euproctis* spp., Yponameutidae such as *Plutella xylostella*, Gelechiidae such as *Pectinophora gossypiella* and *Phthorimaea operculella*, Arctiidae such as *Hyphantria cunea*, and Tineidae such as *Tinea translucens* and *Tineola bisselliella;* noxious insects belonging to order Thripidae: *Thysanoptera* such as *Frankliniella occidentalis, Thrips parmi, Scirtothrips dorsalis, Thrips tabaci, Frankliniella intonsa*, and *Frankliniella fusca;* noxious insects belonging to order Diptera: Agromyzidae such as *Musca domestica, Culexpopiens pallens, Tabanus trigonus, Hylemya antique, Hylemya platura, Anopheles sinensis, Agromyza oryzae, Hydrellia griseola, Chlorops oryzae*, and *Liriomyza trifolii, Dacus cucurbitae*, and *Ceratitis capitata;*

Noxious insects belonging to order Coleoptera: *Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca*, and *Tomicus piniperda;* noxious insects belonging to order Orthoptera: *Locusta migratoria, Gryllotalpa africana, Oxya yezoensis*, and *Oxya japonica;* noxious insects belonging to order Hymenoptera: *Athalia rosae, Acromyrmex* spp., and *Solenopsis* spp.;

noxious insects belonging to order Blattodea: *Blattella germanica, Periplaneta fuliginosa, Periplaneta americana, Periplaneta brunnea*, and *Blatta orientalis*; and noxious insects belonging to order Acarina: Tetranychidae such as *Tetranychus urticae, Panonychus citri*, and *Oligonychus* spp., Eriophyidae such as *Aculops pelekassi*, Tarsonemidae such as *Polyphagotarsonemus latus, Tenuipalpidae, Tuckerellidae*, Acaridae such as *Tyrophagus putrescentiae*, Dermanyssidae such as *Dermatophagoides farina* and *Dermatophagoides ptrenyssnus*, and Cheyletidae such as *Cheyletus eruditus, Cheyletus malaccensis*, and *Cheyletus moorei.*

As the plant pathogens, the following examples can be given.

*Cercospora gossypina, Cercospora kikuchii, Cercospora zeae-maydis, Cercospora sojina, Phakopsora gossypii, Rhizoctonia solani, Colletotrichum gossypii, Peronospora gossypina, Aspergillus* spp., *Penicillium* spp., *Fusarium* spp., *Tricoderma* spp., *Thielaviopsis* spp., *Rhizopus* spp., *Mucor* spp., *Corticium* spp., *Phoma* spp., *Diplodia* spp., *Verticillium* spp., *Puccinia* spp., *Mycosphaerella* spp., *Phytophthora* spp. (for example, *Phytophthora sojae, Phytophthora nicotianae* var. *nicotianae, Phytophthora infestans*, and *Phytophthora erythroseptica*), *Pythium* spp. (for example, *Pythium debaryanum, Pythium sylvaticum, Pythium graminicola, Pythium irregular*, and *Pythium ultimum*), *Microsphaera diffusa, Diaporthe phaseolorum* var.

*sojae, Septoria glycines, Phakopsora pachyrhizi, Sclerotinia sclerotiorum, Elsinoe glycines, Ustilago maydis, Cochliobolus heterostrophus, Gloeocercospora sorghi*, and *Alternaria* spp.

As the weeds, the following examples are given.

Weeds of the family Urticaceae: *Urtica urens;* weeds of the family Polygonaceae: *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicas, Rumex crispus, Rumex obtusifolius*, and *Rumex acetosa;* weeds of the family Portulacaceae: *Portulaca oleracea;* weeds of the family Caryophyllaceae: *Stellaria media, Cerastium holosteoides, Cerastium glomeratum, Spergula arvensis*, and *Silene gallica;* weeds of the family Molluginaceae: *Mollugo verticillata;* weeds of the family Chenopodiaceae: *Chenopodium album, Chenopodium ambrosioides, Kochia scoparia, Salsola kali*, and *Atriplex* spp.;

weeds of the family Amaranthaceae: *Amaranthus retroflexus, Amaranthus viridis, Amaranthus lividus, Amaranthus spinosus, Amaranthus hybridus, Amaranthus palmeri, Amaranthus rudis, Amaranthus patulus, Amaranthus tuberculatos, Amaranthus blitoides, Amaranthus deflexus, Amaranthus quitensis, Alternanthera philoxeroides, Alternanthera sessilis*, and *Alternanthera tenella;* weeds of the family Papaveraceae: *Papaver rhoeas* and *Argemone mexicana;* weeds of the family Brassicaceae: *Raphanus raphanistrum, Raphanus sativus, Sinapis arvensis, Capsella bursa-pastoris, Brassica juncea, Brassica campestris, Descurainia pinnata, Rorippa islandica, Rorippa sylvestris, Thlaspi arvense, Myagrum rugosum, Lepidium virginicum*, and *Coronopus didymus;* weeds of the family Capparaceae: *Cleome affinis;* weeds of the family Fabaceae: *Aeschynomene indica, Aeschynomene rudis, Sesbania exaltata, Cassia obtusifolia, Cassia occidentalis, Desmodium tortuosum, Desmodium adscendens, Trifolium repens, Pueraria lobata, Vicia angustifolia, Indigofera hirsute, Indigofera truxillensis*, and *Vigna sinensis;* weeds of the family Oxalidaceae: *Oxalis corniculata, Oxalis strica*, and *Oxalis oxyptera;* weeds of the family Geraniaceae: *Geranium carolinense* and *Erodium cicutarium;* weeds of the family Euphorbiaceae: *Euphorbia helioscopia, Euphorbia maculate, Euphorbia humistrata, Euphorbia esula, Euphorbia heterophylla, Euphorbia brasiliensis, Acalypha australis, Croton glandulosusi, Croton lobatus, Phyllanthus corcovadensis*, and *Ricinus communis;* weeds of the family Malvaceae: *Abutilon theophrasti, Sida rhombiforia, Sida cordifolia, Sida spinosa, Sida glaziovii, Sida santaremnensis, Hibiscus trionum, Anoda cristata*, and *Malvastrum coromandelianum;* weeds of the family Sterculiaceae: *Waltheria indica;* weeds of the family Violaceae: *Viola arvensis*, and *Viola tricolor;* weeds of the family Cucurbitaceae: *Sicyos angulatus, Echinocystis lobata*, and *Momordica charantia;* weeds of the family Lythraceae: *Lythrum salicaria;* weeds of the family Apiaceae: *Hydrocotyle sibthorpioides;* weeds of the family Sapindaceae: *Cardiospermum halicacabum;* weeds of the family Primulaceae: *Anagallis arvensis;* weeds of the family Asclepiadaceae: *Asclepias syriaca* and *Ampelamus albidus;* weeds of the family Rubiaceae: *Galium aparine, Galium spurium* var. *echinospermon, Spermacoce latifolia, Richardia brasiliensis*, and *Borreria alata;* weeds of the family Convolvulaceae: *Ipomoea nil, Ipomoea hederacea, Ipomoea purpurea, Ipomoea hederacea* var. *integriuscula, Ipomoea lacunose, Ipomoea triloba, Ipomoea acuminate, Ipomoea hederifolia, Ipomoea coccinea, Ipomoea quamoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoids*, and *Jacquemontia tamnifolia;* weeds of the family Boraginaceae: *Myosotis arvensis;* weeds of the family Lamiaceae: *Lamium purpureum, Lamium amplexicaule, Leonotis nepetaefolia, Hyptis suaveolens, Hyptis lophanta, Leonurus sibiricus*, and *Stachys arvensis;* weeds of the family Solanaceae: *Datura stramonium, Solanum nigrum, Solanum americanum, Solanum ptycanthum, Solanum sarrachoides, Solanum rostratum, Solanum aculeatissimum, Solanum sisymbriifolium, Solanum carolinense, Physalis angulata, Physalis subglabrata*, and *Nicandra physaloides;* weeds of the family Scrophulariaceae: *Veronica hederaefolia, Veronica persica*, and *Veronica arvensis;* weeds of the family Plantaginaceae: *Plantago asiatica;* weeds of the family Asteraceae: *Xanthium pensylvanicum, Xanthium occidentale, Helianthus annuus, Matricaria chamomilla, Matricaria perforate, Chrysanthemum segetum, Matricaria matricarioides, Artemisia princeps, Artemisia vulgaris, Artemisia verlotorum, Solidago altissima, Taraxacum officinale, Galinsoga ciliate, Galinsoga parviflora, Senecio vulgaris, Senecio brasiliensis, Senecio grisebachii, Conyza bonariensis, Conyza Canadensis, Ambrosia artemisiaefolia, Ambrosia trifida, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blainvillea latifolia, Tridax procumbens, Porophyllum ruderale, Acanthospermum australe, Acanthospermum hispidum, Cardiospermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium hysterophorus, Siegesbeckia orientalis*, and *Soliva sessilis;* weeds of the family Liliaceae: *Allium canadense* and *Allium vineale;* weeds of the family Commelinaceae: *Commelina communis, Commelina bengharensis*, and *Commelina erecta;* weeds of the family Poaceae: *Echinochloa crus-galli, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Alospecurus aequalis, Alopecurus myosuroides, Avena fatua, Sorghum halepense, Sorghum vulgare, Agropyron repens, Lolium multiflorum, Lolium perenne, Lolium rigidum, Bromus secalinus, Bromus tectorum, Hordeum jubatum, Aegilops cylindrica, Phalaris arundinacea, Phalaris minor, Apera spica-venti, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Eragrostis pilosa, Rhynchelitrum repens, Dactyloctenium aegyptium, Ischaemum rugosum, Oryza sativa, Paspalum notatum, Paspalum maritimum, Pennisetum clandestinum, Pennisetum setosum*, and *Rottboellia cochinchinensis;* weeds of the family Cyperaceae: *Cyperus microiria, Cyperus iria, Cyperus odoratus, Cyperus rotundus, Cyperus esculentus*, and *Kyllinga gracillima*; and weeds of the family Equisetaceae: *Equisetum arvense* and *Equisetum palustre*.

In the method of the present invention, one or more other agrochemicals may be used in combination with the compounds of the group B or the A-type crystal flumioxazin either simultaneously or separately. Examples of the other agrochemicals include insecticides, acaricides, nematicides, fungicides, herbicides, plant growth regulators, and safeners.

As the above herbicides, plant growth regulators, and safeners, the following examples are given.

Herbicides: pyrithiobac, pyrithiobac-sodium salt, pyriminobac, pyriminobac-methyl, bispyribac, bispyribac-sodium salt, pyribenzoxim, pyrimisulfan, pyriftalid, triafamone, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, metazosulfuron, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron-sodium salt, trifloxysulfuron, chlorsulfuron, cinosulfuron, ethametsulfuron, ethametsulfuron-methyl, iodosulfuron, iodosulfuron-methyl-sodium, iofensulfuron, iofensulfuron-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, bencarbazone, flucarbazone, flucarbazone-sodium salt, ipfencarbazone, propoxycarbazone, propoxycarbazone-sodium salt, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium salt, imazapic, imazapic-ammonium salt, imazapyr, imazapyr-isopropyl-ammonium salt, imazaquin, imazaquin-ammonium salt, imazethapyr, imazethapyr-ammonium salt, clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, pinoxaden, azafenidin, oxadiazon, oxadiargyl, carfentrazone, carfentrazone-ethyl, saflufenacil, cinidon, cinidon-ethyl, sulfentrazone, pyraclonil, pyraflufen, pyraflufen-ethyl, butafenacil, fluazolate, fluthiacet, fluthiacet-methyl, flufenpyr, flufenpyr-ethyl, flumiclorac, flumiclorac-pentyl, pentoxazone, oxyfluorfen, acifluorfen, aclonifen, chlomethoxynil, chloronitrofen, nitrofen, bifenox, fluoroglycofene, fluoroglycofene-ethyl, fomesafen, fomesafen-sodium salt, lactofen, compounds represented by the following formula (II):

Formula (II)

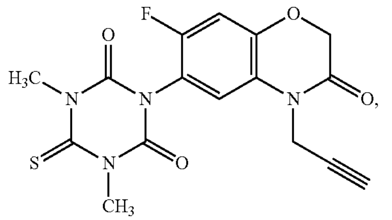

(II)

benzobicyclon, bicyclopyrone, mesotrione, sulcotrione, tefuryltrione, tembotrione, isoxachlortole, isoxaflutole, benzofenap, pyrasulfotole, pyrazolynate, pyrazoxyfen, topramezone, diflufenican, picolinafen, beflubutamid, norflurazon, fluridone, flurochloridone, flurtamone, ioxynil, ioxyniloctanoate, bentazone, pyridate, bromoxynil, bromoxynil octanoate, chlorotoluron, dimefuron, diuron, linuron, fluometuron, isoproturon, isouron, tebuthiuron, benzthiazuron, methabenzthiazuron, propanil, metobromuron, metoxuron, monolinuron, siduron, simazine, atrazine, propazine, cyanazine, ametryn, simetryn, dimethametryn, prometryn, terbumeton, terbuthylazine, terbutryn, trietazine, hexazinone, metamitron, metribuzin, amicarbazone, bromacil, lenacil, terbacil, chloridazon, desmedipham, phenmedipham, propachlor, metazachlor, alachlor, acetochlor, metolachlor, S-metolachlor, butachlor, pretilachlor, thenylchlor, indanofan, cafenstrole, fentrazamide, dimethenamid, dimethenamid-P, mefenacet, pyroxasulfone, fenoxasulfone, naproanilide, anilofos, flufenacet, trifluralin, pendimethalin, ethafluralin, benfluralin, prodiamine, indaziflam, triaziflam, butamifos, dithiopyr, thiazopyr, dicamba and a salt thereof (diglycolamine salt, dimethylammonium salt, isopropylammonium salt, potassium salt, sodium salt, and choline salt), 2,4-D and a salt or ester thereof (butotyl ester, dimethylammonium salt, diolamine salt, ethylhexyl ester, isooctyl ester, isopropylammonium salt, sodium salt, and triisopropanolamine salt), 2,4-DB and a salt or ester thereof (dimethylammonium salt, isooctyl ester, and choline salt), MCPA and a salt or ester thereof (dimethylammonium salt, 2-ethylhexylester, isooctyl ester, sodium salt, and choline salt), MCPB, mecoprop and a salt or ester thereof (dimethylammonium salt, diolamine salt, ethadyl ester, 2-ethylhexyl ester, isooctyl ester, methyl ester, potassium salt, sodium salt, tololamine salt, and choline salt), mecoprop-P and a salt or ester thereof (dimethylammonium salt, 2-ethylhexyl ester, isobutyl salt, potassium salt, and choline salt), dichlorprop and a salt or ester thereof (butotyl ester, dimethylammonium salt, 2-ethylhexyl ester, isooctyl ester, methyl ester, potassium salt, sodium salt, and choline salt), dichlorprop-P, dichlorprop-P dimethylammonium salt, triclopyr and a salt or ester thereof (butotyl ester and triethylammonium salt), fluroxypyr, fluroxypyr-meptyl, picloram and a salt thereof (potassium salt, triisopanolammonium salt, and choline salt), quinclorac, quinmerac, aminopyralid and a salt thereof (potassium salt, triisopanolammonium salt, and choline salt), clopyralid and a salt thereof (olamine salt, potassium salt, triethylammonium salt, and choline salt), clomeprop, glufosinate, glufosinate-ammonium salt, glufosinate-P, glufosinate-P-sodium salt, bialaphos, isoxaben, dichlobenil, methiozolin, diallate, butylate, triallate, chlorpropham, asulam, phenisopham, benthiocarb, molinate, esprocarb, pyributicarb, prosulfocarb, orbencarb, EPTC, dimepiperate, swep, aminocyclopyrachlor, aminocyclopyrachlor-methyl, aminocyclopyrachlor-potassium, difenoxuron, methyl dymron, bromobutide, dymron, cumyluron, diflufenzopyr, etobenzanide, tridiphane, amitrole, fenchlorazole, clomazone, maleic acid hydrazide, oxaziclomefone, cinmethylin, benfuresate, ACN, dalapon, chlorthiamid, flupoxam, bensulide, paraquat, paraquat-dichloride, diquat, and diquat-dibromide.

Plant growth regulators: hymexazol, paclobutrazol, uniconazole, uniconazole-P, inabenfide, prohexadione-calcium, 1-methylcyclopropene, and trinexapac.

Safeners: benoxacor, cloquintocet, cloquintocet-mexyl, cyometrinil, cyprosulfamide, dichlormid, dicyclonon, dietholate, fenchlorazole, fenchlorazole-ethyl, fenclorim, flurazole, fluxofenim, furilazole, isoxadifen, isoxadifen-ethyl, mefenpyr, mefenpyr-diethyl, mephenate, naphthalic anhydride, and oxabetrinil.

In the method of the present invention, a glufosinate-ammonium salt, chlorimuron-ethyl, cloransulam-methyl, pyroxasulfone, imazethapyr-ammonium salt, metribuzin, 2,4-D,2,4-D-butotyl ester, 2,4-D-dimethylammonium salt, 2,4-D-diolamine salt, 2,4-D-ethylhexyl ester, 2,4-D-isooctyl ester, 2,4-D-isopropylammonium salt, 2,4-D-sodium salt, 2,4-D-triisopropanolamine salt, dicamba, dicamba-diglycolamine salt, dicamba-dimethylammonium salt, dicamba-isopropylammonium salt, dicamba-potassium salt, dicamba-sodium salt, dicamba-choline salt, mesotrione, tembotrione, isoxaflutole, and ametryn are particularly preferable as the herbicides which may be simultaneously used in combination with the A-type crystal flumioxazin.

In the present invention, cyprosulfamide, mefenpyr-diethyl, and isoxadifen-ethyl are particularly preferable as the safener which may be simultaneously used in combination with the A-type crystal flumioxazin.

The followings are more preferable as the combinations of the herbicide and/or safener which may be used in combination with the A-type crystal flumioxazin:

a combination of A-type crystal flumioxazin and glufosinate-ammonium salt;

a combination of A-type crystal flumioxazin and chlorimuron-ethyl;

a combination of A-type crystal flumioxazin and cloransulam-methyl;

a combination of A-type crystal flumioxazin, chlorimuron-ethyl, and pyroxasulfone;

a combination of A-type crystal flumioxazin and pyroxasulfone;

a combination of A-type crystal flumioxazin and imazethapyr-ammonium salt;

a combination of A-type crystal flumioxazin and metribuzin;

a combination of A-type crystal flumioxazin and 2,4-D;

a combination of A-type crystal flumioxazin and 2,4-D-butotyl ester;

a combination of A-type crystal flumioxazin and 2,4-D-dimethylammonium salt;

a combination of A-type crystal flumioxazin and 2,4-D-diolamine salt;

a combination of A-type crystal flumioxazin and 2,4-D-ethylhexyl ester;

a combination of A-type crystal flumioxazin and 2,4-D-isooctyl ester;

a combination of A-type crystal flumioxazin and 2,4-D-isopropylammonium salt;

a combination of A-type crystal flumioxazin and 2,4-D-sodium salt;

a combination of A-type crystal flumioxazin and 2,4-D-triisopropanolamine salt;

a combination of A-type crystal flumioxazin and dicamba;

a combination of A-type crystal flumioxazin and dicamba-diglycolamine salt;

a combination of A-type crystal flumioxazin and dicamba-dimethylammonium salt;

a combination of A-type crystal flumioxazin and dicamba-isopropylammonium salt;

a combination of A-type crystal flumioxazin and dicamba-potassium salt;

a combination of A-type crystal flumioxazin and dicamba-sodium salt;

a combination of A-type crystal flumioxazin and dicamba-choline salt;

a combination of A-type crystal flumioxazin, dicamba, and isoxadifen-ethyl;

a combination of A-type crystal flumioxazin, dicamba-diglycolamine salt, and isoxadifen-ethyl;

a combination of A-type crystal flumioxazin, dicamba-dimethylammonium salt, and isoxadifen-ethyl;

a combination of A-type crystal flumioxazin, dicamba-isopropylammonium salt, and isoxadifen-ethyl;

a combination of A-type crystal flumioxazin, dicamba-potassium salt, and isoxadifen-ethyl;

a combination of A-type crystal flumioxazin, dicamba-sodium salt, and isoxadifen-ethyl;

a combination of A-type crystal flumioxazin, dicamba-choline salt, and isoxadifen-ethyl;

a combination of A-type crystal flumioxazin and mesotrione;

a combination of A-type crystal flumioxazin and tembotrione;

a combination of A-type crystal flumioxazin and isoxaflutole;

a combination of A-type crystal flumioxazin and ametryn;

a combination of A-type crystal flumioxazin, isoxaflutole, and cyprosulfamide;

a combination of A-type crystal flumioxazin, tembotrione, and isoxadifen; and a combination of A-type crystal flumioxazin and saflufenacil.

EXAMPLES

Hereinbelow, the present invention will be described in detail byway of examples, but the present invention is not limited to these examples.

Production Example

Production Example of A-type crystal flumioxazin used in the method of the present invention will be shown below.

Production Example 1

Example 1

Flumioxazin (100 mg) was dissolved in methylisobutylketone at 60° C. so as to adjust its concentration to 10.1 mg/mL. The solvent was rapidly cooled to 0° C., followed by being left to stand to obtain A-type crystals.

By X'Pert Pro MPD (manufactured by Nederland PANalytical B.V.), a powder X-ray diffraction pattern of the obtained crystals was measured for each crystal at a scanning range from 2.0° to 40.0° (2θ) using CuKα rays (40 kV, 30 mA).

The pattern of the obtained crystals had the peaks with as 2θ values as shown in Table 2.

TABLE 2

| 2θ value (°) | d value (Å) | Relative intensity (%) |
|---|---|---|
| 9.8 | 9.0179 | 61.1 |
| 11.4 | 7.7556 | 13.1 |
| 12.7 | 6.9645 | 100.0 |
| 13.8 | 6.4117 | 24.1 |
| 16.0 | 5.5347 | 37.9 |
| 16.4 | 5.4006 | 32.4 |
| 16.7 | 5.3042 | 29.1 |

Test Examples

First, given are the standard of evaluation of a pest control effect (harmful arthropod control effect, plant pathogen control effect, and herbicidal effect) and that of crop injuries, which will be shown in examples hereinafter.

[Harmful Arthropod Control Effect]

In the evaluation of the harmful arthropod control effect, each insect at the time of investigation is examined by discriminating whether the insect is alive or dead to calculate a controlling value by the following equation.

$$\text{Controlling value (\%)} = 100 \times (1 - T/C)$$

wherein C represents the number of insects to be observed in an untreated area, and T represents the number of insects to be observed in a treated area

[Plant Pathogen Control Effect]

In the evaluation of the plant pathogen control effect, the symptom of each test plant in a treated area is compared with that in an untreated area and when there is no or almost no difference in symptom between the treated area and the untreated area at the time of investigation, the case is given “0”, and when no or almost no change in symptom caused by plant pathogens is observed at the time of investigation, the case is given “100”, thereby grading each sample between 0 to 100.

[Herbicidal Effect and Crop Injuries]

In the evaluation of the herbicidal effect, the germination or growth condition of each test weed in a treated area is compared with that in an untreated area and when there is no or almost no difference in germination or growth condition between the treated area and the untreated area at the time of investigation, the case is given “0”, and when the test plant perfectly withers and dies, or the germination or growth of the plant is perfectly restricted at the time of investigation, the case is given “100”, thereby grading each sample between 0 to 100.

In the evaluation of crop injuries, the case where almost no crop injury is observed is expressed as “harmless”, the case where mild crop injuries are observed is expressed as “small”, the case where moderate crop injuries are observed is expressed as “middle”, and the case where severe crop injuries are observed is expressed as “large”.

Example 1

A pot is filled with soil and weeds are sowed, and the surface of the soil is uniformly treated with A-type crystal flumioxazin at a dose of 25, 50, 100, or 200 g/ha. After 15 days, cotton seeds are sowed to which one or more compounds selected from the group B are attached at a dose of 1, 10, or 100 g/100 kg seeds. This pot is placed in a greenhouse. The pest control effect and crop injuries are examined 15 days after the seeds are sowed.

Example 2

One or more compounds selected from the group B are attached to cotton seeds at a dose of 1, 10, or 100 g/100 kg seeds. Next, the seeds are sowed in a cultivated field. Stem leaves of the weed are directly treated with A-type crystal flumioxazin at a dose of 25, 50, 100, 200, or 400 g/ha in the condition of the cotton main stem being lignified at a length of 15 cm from the surface of the ground 30 days after these seeds are sowed. The pest control effect and crop injuries are examined 28 days after the treatment.

Example 3

A pot is filled with soil and weeds are sowed, and the surface of the soil is uniformly treated with A-type crystal flumioxazin at a dose of 25, 50, 100, or 200 g/ha. After 7 days, soybean seeds are sowed to which one or more compounds selected from the group B are attached at a dose of 1, 10, or 100 g/100 kg seeds. This pot is placed in a greenhouse. The pest control effect and crop injuries are examined 15 days after the seeds are sowed.

Example 4

One or more compounds selected from the group B are attached to soybean seeds at a dose of 1, 10, or 100 g/100 kg seeds. Next, a pot is filled with soil and the soybean seeds and weed seeds are sowed. On the day of sowing, the surface of the soil is uniformly treated with A-type crystal flumioxazin at a dose of 25, 50, 100, or 200 g/ha. This pot is placed in a greenhouse. The pest control effect and crop injuries are examined 15 days after the seeds are sowed.

Example 5

A pot is filled with soil and weeds are sowed, and the surface of the soil is uniformly treated with A-type crystal flumioxazin at a dose of 25, 50, 100, or 200 g/ha. After 7 days, corn seeds are sowed to which one or more compounds selected from the group B are attached at a dose of 1, 10, or 100 g/100 kg seeds. This pot is placed in a greenhouse. The pest control effect and crop injuries are examined 15 days after the seeds are sowed.

Example 6

One or more compounds selected from the group B are attached to corn seeds at a dose of 1, 10, or 100 g/100 kg seeds. Next, a pot is filled with soil and the corn seeds and weed seeds are sowed. On the day of sowing, the surface of the soil is uniformly treated with A-type crystal flumioxazin at a dose of 25, 50, 100, or 200 g/ha. This pot is placed in a greenhouse. The pest control effect and crop injuries are examined 15 days after the seeds are sowed.

Example 7

A pot is filled with soil and weeds are sowed, and the surface of the soil is uniformly treated with A-type crystal flumioxazin at a dose of 25, 50, 100, or 200 g/ha. After 15 days, wheat seeds are sowed to which one or more compounds selected from the group B are attached at a dose of 1, 10, or 100 g/100 kg seeds. This pot is placed in a greenhouse. The pest control effect and crop injuries are examined 15 days after the seeds are sowed.

Example 8

A pot is filled with soil and weeds are sowed, and the surface of the soil is uniformly treated with A-type crystal flumioxazin at a dose of 25, 50, 100, or 200 g/ha. After 15 days, tomato seeds are sowed to which one or more compounds selected from the group B are attached at a dose of 1, 10, or 100 g/100 kg seeds. This pot is placed in a greenhouse. The pest control effect and crop injuries are examined 15 days after the tomato seeds are sowed.

Example 9

A pot is filled with soil and weeds are sowed, and the surface of the soil is uniformly treated with A-type crystal flumioxazin at a dose of 25, 50, 100, or 200 g/ha. After 15 days, eggplant seeds are sowed to which one or more compounds selected from the group B are attached at a dose of 1, 10, or 100 g/100 kg seeds. This pot is placed in a greenhouse. The pest control effect and crop injuries are examined 15 days after the eggplant seeds are sowed.

Example 10

A pot is filled with soil and weeds are sowed, and the surface of the soil is uniformly treated with A-type crystal flumioxazin at a dose of 25, 50, 100, or 200 g/ha. After 15 days, bell pepper seeds are sowed to which one or more compounds selected from the group B are attached at a dose of 1, 10, or 100 g/100 kg seeds. This pot is placed in a greenhouse. The pest control effect and crop injuries are examined 15 days after the bell pepper seeds are sowed.

Example 11

A pot is filled with soil and weeds are sowed, and the surface of the soil is uniformly treated with A-type crystal flumioxazin at a dose of 25, 50, 100, 200, or 400 g/ha. After 15 days, sugar cane stem fragments are planted to which one or more compounds selected from the group B at a dose of 1, 10, or 100 g/100 kg stem fragments. This pot is placed in a greenhouse. The pest control effect and crop injuries are examined 15 days after the sugar cane stem fragments are planted.

Example 12

A pot is filled with soil and weeds are sowed, and the surface of the soil is uniformly treated with A-type crystal flumioxazin at a dose of 25, 50, 100, or 200 g/ha. After 15 days, common bean seeds are sowed to which one or more compounds selected from the group B are attached at a dose of 1, 10, or 100 g/100 kg seeds. This pot is placed in a greenhouse. The pest control effect and crop injuries are examined 15 days after the common bean seeds are sowed.

Example 13

A pot is filled with soil and weeds are sowed, and the surface of the soil is uniformly treated with A-type crystal flumioxazin at a dose of 25, 50, 100, or 200 g/ha. After 15 days, rice seeds are sowed to which one or more compounds selected from the group B are attached at a dose of 1, 10, or 100 g/100 kg seeds. This pot is placed in a greenhouse. The pest control effect and crop injuries are examined 15 days after the rice seeds are sowed.

Example 14

A pot is filled with soil and weeds are sowed, and the surface of the soil is uniformly treated with A-type crystal flumioxazin at a dose of 25, 50, 100, or 200 g/ha. After 15 days, rapeseeds are sowed to which one or more compounds selected from the group B are attached at a dose of 1, 10, or 100 g/100 kg seeds. This pot is placed in a greenhouse. The pest control effect and crop injuries are examined 15 days after the rapeseeds are sowed.

Example 15

One or more compounds selected from the group B are attached to sugar cane stem fragments at a dose of 1, 10, or 100 g/100 kg stem fragments. Then, the stem fragments are planted in a cultivated field. When the plant height of the sugar cane becomes 60 cm or higher after the stem fragments are planted, stem leaves of the weed are directly treated with A-type crystal flumioxazin at a dose of 25, 50, 100, 200, or 400 g/ha. The pest control effect and crop injuries are examined 28 days after the treatment.

Example 16

One or more compounds selected from the group B are attached to peanut seeds at a dose of 1, 10, or 100 g/100 kg seeds. Next, a pot is filled with soil and the peanut seeds and weed seeds are sowed. On the day of sowing, the surface of the soil is uniformly treated with A-type crystal flumioxazin at a dose of 25, 50, 100, or 200 g/ha. This pot is placed in a greenhouse. The pest control effect and crop injuries are examined 15 days after the seeds are sowed.

Example 17

One or more compounds selected from the group B are attached to common bean seeds at a dose of 1, 10, or 100 g/100 kg seeds. Next, a pot is filled with soil and the common bean seeds and weed seeds are sowed. On the day of sowing, the surface of the soil is uniformly treated with A-type crystal flumioxazin at a dose of 25, 50, 100, or 200 g/ha. This pot is placed in a greenhouse. The pest control effect and crop injuries are examined 15 days after the seeds are sowed.

Example 18

One or more compounds selected from the group B are attached to pea seeds at a dose of 1, 10, or 100 g/100 kg seeds. Next, a pot is filled with soil and the pea seeds and weed seeds are sowed. On the day of sowing, the surface of the soil is uniformly treated with A-type crystal flumioxazin at a dose of 25, 50, 100, or 200 g/ha. This pot is placed in a greenhouse. The pest control effect and crop injuries are examined 15 days after the seeds are sowed.

Example 19

One or more compounds selected from the group B are attached to sunflower seeds at a dose of 1, 10, or 100 g/100 kg seeds. Next, a pot is filled with soil and the sunflower seeds and weed seeds are sowed. On the day of sowing, the surface of the soil is uniformly treated with A-type crystal flumioxazin at a dose of 25, 50, 100, or 200 g/ha. This pot is placed in a greenhouse. The pest control effect and crop injuries are examined 15 days after the seeds are sowed.

Example 20

One or more compounds selected from the group B are attached to sugar cane stem fragments at a dose of 1, 10, or 100 g/100 kg stem fragments. Next, a pot is filled with soil, then weed seeds are sowed and the stem fragments are planted. On the day of sowing and planting, the surface of the soil is uniformly treated with A-type crystal flumioxazin at a dose of 25, 50, 100, 200, or 400 g/ha. This pot is placed in a greenhouse. The pest control effect and crop injuries are examined 15 days after sowing and planting.

Example 21

One or more compounds selected from the group B are attached to potato tubers at a dose of 1, 10, or 100 g/100 kg tubers. Next, a pot is filled with soil, then weed seeds are sowed and the tubers are planted. On the day of sowing and planting, the surface of the soil is uniformly treated with A-type crystal flumioxazin at a dose of 12.5, 25, 50, or 100 g/ha. This pot is placed in a greenhouse. The pest control effect and crop injuries are examined 15 days after sowing and planting.

Example 22

One or more compounds selected from the group B are attached to onion seeds at a dose of 1, 10, or 100 g/100 kg seeds. Next, a pot is filled with soil and the onion seeds and weed seeds are sowed. This pot is placed in a greenhouse. When the onion grows 2 to 6 leaves, the surface of the soil and stem leaves of the weeds are uniformly treated with A-type crystal flumioxazin at a dose of 12.5, 25, 50, or 100 g/ha. The pest control effect and crop injuries are examined 15 days after the treatment with A-type crystal flumioxazin.

Example 23

One or more compounds selected from the group B are attached to garlic bulbs at a dose of 1, 10, or 100 g/100 kg bulbs. Next, a pot is filled with soil, then weed seeds are sowed and the bulbs are planted. On the day of sowing and planting, the surface of the soil is uniformly treated with A-type crystal flumioxazin at a dose of 50, 100, 200, or 400 g/ha. This pot is placed in a greenhouse. The pest control effect and crop injuries are examined 15 days after sowing and planting.

Example 24

One or more compounds selected from the group B are attached to sunflower seeds at a dose of 1, 10, or 100 g/100 kg seeds. Next, a pot is filled with soil and the sunflower seeds and weed seeds are sowed. This pot is placed in a greenhouse. When the sunflower grows 2 to 6 leaves, the surface of the soil and stem leaves of the weeds are uniformly treated with A-type crystal flumioxazin at a dose of 12.5, 25, 50, or 100 g/ha. The pest control effect and crop injuries are examined 15 days after the treatment with A-type crystal flumioxazin.

Example 25

One or more compounds selected from the group B are attached to wheat seeds at a dose of 1, 10, or 100 g/100 kg seeds. Next, a pot is filled with soil and the wheat seeds and weed seeds are sowed. This pot is placed in a greenhouse. When the wheat grows 2 to 6 leaves, the surface of the soil and stem leaves of the weeds are uniformly treated with A-type crystal flumioxazin at a dose of 12.5, 25, 50, or 100 g/ha. The pest control effect and crop injuries are examined 15 days after the treatment with A-type crystal flumioxazin.

Example 26

Each of combinations of compounds selected from the combinations shown in Tables 3, 4 and 5 is attached to soybean seeds, corn seeds, or cotton seeds at a dose of 1, 10, or 100 g/100 kg seeds. Next, a pot is filled with soil and the crop seeds and weed seeds are sowed. On the day of sowing, the surface of the soil is uniformly treated with A-type crystal flumioxazin at a dose of 25, 50, 100, 200, or 400 g/ha. This pot is placed in a greenhouse. The pest control effect and crop injuries are examined 15 days after the treatment with A-type crystal flumioxazin.

Example 27

Each of combinations of compounds selected from the combinations shown in Tables 3, 4 and 5 is attached to cotton seeds at a dose of 1, 10, or 100 g/100 kg seeds. Next, a pot is filled with soil and the cotton seeds and weed seeds are sowed. The surface of the soil and stem leaves of the weeds are uniformly treated with A-type crystal flumioxazin at a dose of 25, 50, 100, 200, or 400 g/ha in the condition of the cotton main stem being lignified at a length of 15 cm from the surface of the ground 30 days after these seeds are sowed. This pot is placed in a greenhouse. The pest control effect and crop injuries are examined 15 days after the treatment with A-type crystal flumioxazin.

TABLE 3

| Number of combination | Combinations of compounds | |
|---|---|---|
| 1-1 | Clothianidin | Ipconazole |
| 1-2 | Clothianidin | Metconazole |
| 1-3 | Clothianidin | Diphenoconazole |
| 1-4 | Clothianidin | Tebuconazole |
| 1-5 | Clothianidin | Prothioconazole |
| 1-6 | Clothianidin | Fluquinconazole |
| 1-7 | Clothianidin | Triticonazole |
| 1-8 | Clothianidin | Imazalil |
| 1-9 | Clothianidin | Pencycuron |
| 1-10 | Clothianidin | Prochloraz |
| 1-11 | Clothianidin | Pyraclostrobin |
| 1-12 | Clothianidin | Azoxystrobin |
| 1-13 | Clothianidin | Trifloxystrobin |
| 1-14 | Clothianidin | Metalaxyl |
| 1-15 | Clothianidin | Metalaxyl-M |
| 1-16 | Clothianidin | Fludioxonil |
| 1-17 | Clothianidin | Thiram |
| 1-18 | Clothianidin | Mancozeb |
| 1-19 | Clothianidin | Flutolanil |
| 1-20 | Clothianidin | Sedaxane |
| 1-21 | Clothianidin | Penflufen |
| 1-22 | Clothianidin | Fluxapyroxad |
| 1-23 | Clothianidin | *Bacillus firmus* |
| 1-24 | Clothianidin | *Pasteuria penetrans* |
| 1-25 | Clothianidin | Abamectin |
| 1-26 | Clothianidin | Thiodicarb |
| 1-27 | Clothianidin | Tolclophos-methyl |
| 1-28 | Clothianidin | Ethaboxam |
| 1-29 | Clothianidin | Compound 4 |
| 1-30 | Clothianidin | Compound 2 |
| 1-31 | Clothianidin | Compound 3 |
| 1-32 | Clothianidin | Compound 1 |
| 1-33 | Clothianidin | Compound 5 |
| 1-34 | Clothianidin | Orysastrobin |
| 1-35 | Clothianidin | Isotianil |
| 1-36 | Clothianidin | Probenazole |
| 1-37 | Clothianidin | Diclocymet |
| 1-38 | Clothianidin | Furametpyr |
| 1-39 | Imidacloprid | Ipconazole |
| 1-40 | Imidacloprid | Metconazole |
| 1-41 | Imidacloprid | Diphenoconazole |
| 1-42 | Imidacloprid | Tebuconazole |
| 1-43 | Imidacloprid | Prothioconazole |
| 1-44 | Imidacloprid | Fluquinconazole |
| 1-45 | Imidacloprid | Triticonazole |
| 1-46 | Imidacloprid | Imazalil |
| 1-47 | Imidacloprid | Pencycuron |
| 1-48 | Imidacloprid | Prochloraz |
| 1-49 | Imidacloprid | Pyraclostrobin |
| 1-50 | Imidacloprid | Azoxystrobin |
| 1-51 | Imidacloprid | Trifloxystrobin |
| 1-52 | Imidacloprid | Metalaxyl |
| 1-53 | Imidacloprid | Metalaxyl-M |
| 1-54 | Imidacloprid | Fludioxonil |

TABLE 3-continued

| Number of combination | Combinations of compounds | |
|---|---|---|
| 1-55 | Imidacloprid | Thiram |
| 1-56 | Imidacloprid | Mancozeb |
| 1-57 | Imidacloprid | Flutolanil |
| 1-58 | Imidacloprid | Sedaxane |
| 1-59 | Imidacloprid | Penflufen |
| 1-60 | Imidacloprid | Fluxapyroxad |
| 1-61 | Imidacloprid | *Bacillus firmus* |
| 1-62 | Imidacloprid | *Pasteuria penetrans* |
| 1-63 | Imidacloprid | Abamectin |
| 1-64 | Imidacloprid | Thiodicarb |
| 1-65 | Imidacloprid | Tolclophos-methyl |
| 1-66 | Imidacloprid | Ethaboxam |
| 1-67 | Imidacloprid | Compound 4 |
| 1-68 | Imidacloprid | Compound 2 |
| 1-69 | Imidacloprid | Compound 3 |
| 1-70 | Imidacloprid | Compound 1 |
| 1-71 | Imidacloprid | Compound 5 |
| 1-72 | Imidacloprid | Orysastrobin |
| 1-73 | Imidacloprid | Isotianil |
| 1-74 | Imidacloprid | Probenazole |
| 1-75 | Imidacloprid | Diclocymet |
| 1-76 | Imidacloprid | Furametpyr |
| 1-77 | Thiamethoxam | Ipconazole |
| 1-78 | Thiamethoxam | Metconazole |
| 1-79 | Thiamethoxam | Diphenoconazole |
| 1-80 | Thiamethoxam | Tebuconazole |
| 1-81 | Thiamethoxam | Prothioconazole |
| 1-82 | Thiamethoxam | Fluquinconazole |
| 1-83 | Thiamethoxam | Triticonazole |
| 1-84 | Thiamethoxam | Imazalil |
| 1-85 | Thiamethoxam | Pencycuron |
| 1-86 | Thiamethoxam | Prochloraz |
| 1-87 | Thiamethoxam | Pyraclostrobin |
| 1-88 | Thiamethoxam | Azoxystrobin |
| 1-89 | Thiamethoxam | Trifloxystrobin |
| 1-90 | Thiamethoxam | Metalaxyl |
| 1-91 | Thiamethoxam | Metalaxyl-M |
| 1-92 | Thiamethoxam | Fludioxonil |
| 1-93 | Thiamethoxam | Thiram |
| 1-94 | Thiamethoxam | Mancozeb |
| 1-95 | Thiamethoxam | Flutolanil |
| 1-96 | Thiamethoxam | Sedaxane |
| 1-97 | Thiamethoxam | Penflufen |
| 1-98 | Thiamethoxam | Fluxapyroxad |
| 1-99 | Thiamethoxam | *Bacillus firmus* |
| 1-100 | Thiamethoxam | *Pasteuria penetrans* |
| 1-101 | Thiamethoxam | Abamectin |
| 1-102 | Thiamethoxam | Thiodicarb |
| 1-103 | Thiamethoxam | Tolclophos-methyl |
| 1-104 | Thiamethoxam | Ethaboxam |
| 1-105 | Thiamethoxam | Compound 4 |
| 1-106 | Thiamethoxam | Compound 2 |
| 1-107 | Thiamethoxam | Compound 3 |
| 1-108 | Thiamethoxam | Compound 1 |
| 1-109 | Thiamethoxam | Compound 5 |
| 1-110 | Thiamethoxam | Orysastrobin |
| 1-111 | Thiamethoxam | Isotianil |
| 1-112 | Thiamethoxam | Probenazole |
| 1-113 | Thiamethoxam | Diclocymet |
| 1-114 | Thiamethoxam | Furametpyr |
| 1-115 | Beta-cyfluthrin | Ipconazole |
| 1-116 | Beta-cyfluthrin | Metconazole |
| 1-117 | Beta-cyfluthrin | Diphenoconazole |
| 1-118 | Beta-cyfluthrin | Tebuconazole |
| 1-119 | Beta-cyfluthrin | Prothioconazole |
| 1-120 | Beta-cyfluthrin | Fluquinconazole |
| 1-121 | Beta-cyfluthrin | Triticonazole |
| 1-122 | Beta-cyfluthrin | Imazalil |
| 1-123 | Beta-cyfluthrin | Pencycuron |
| 1-124 | Beta-cyfluthrin | Prochloraz |
| 1-125 | Beta-cyfluthrin | Pyraclostrobin |
| 1-126 | Beta-cyfluthrin | Azoxystrobin |
| 1-127 | Beta-cyfluthrin | Trifloxystrobin |
| 1-128 | Beta-cyfluthrin | Metalaxyl |
| 1-129 | Beta-cyfluthrin | Metalaxyl-M |
| 1-130 | Beta-cyfluthrin | Fludioxonil |
| 1-131 | Beta-cyfluthrin | Thiram |

TABLE 3-continued

| Number of combination | Combinations of compounds | |
|---|---|---|
| 1-132 | Beta-cyfluthrin | Mancozeb |
| 1-133 | Beta-cyfluthrin | Flutolanil |
| 1-134 | Beta-cyfluthrin | Sedaxane |
| 1-135 | Beta-cyfluthrin | Penflufen |
| 1-136 | Beta-cyfluthrin | Fluxapyroxad |
| 1-137 | Beta-cyfluthrin | *Bacillus firmus* |
| 1-138 | Beta-cyfluthrin | *Pasteuria penetrans* |
| 1-139 | Beta-cyfluthrin | Abamectin |
| 1-140 | Beta-cyfluthrin | Thiodicarb |
| 1-141 | Beta-cyfluthrin | Tolclophos-methyl |
| 1-142 | Beta-cyfluthrin | Ethaboxam |
| 1-143 | Beta-cyfluthrin | Compound 4 |
| 1-144 | Beta-cyfluthrin | Compound 2 |
| 1-145 | Beta-cyfluthrin | Compound 3 |
| 1-146 | Beta-cyfluthrin | Compound 1 |
| 1-147 | Beta-cyfluthrin | Compound 5 |
| 1-148 | Abamectin | Ipconazole |
| 1-149 | Abamectin | Metconazole |
| 1-150 | Abamectin | Diphenoconazole |
| 1-151 | Abamectin | Tebuconazole |
| 1-152 | Abamectin | Prothioconazole |
| 1-153 | Abamectin | Fluquinconazole |
| 1-154 | Abamectin | Triticonazole |
| 1-155 | Abamectin | Imazalil |
| 1-156 | Abamectin | Pencycuron |
| 1-157 | Abamectin | Prochloraz |
| 1-158 | Abamectin | Pyraclostrobin |
| 1-159 | Abamectin | Azoxystrobin |
| 1-160 | Abamectin | Trifloxystrobin |
| 1-161 | Abamectin | Metalaxyl |
| 1-162 | Abamectin | Metalaxyl-M |
| 1-163 | Abamectin | Fludioxonil |
| 1-164 | Abamectin | Thiram |
| 1-165 | Abamectin | Mancozeb |
| 1-166 | Abamectin | Flutolanil |
| 1-167 | Abamectin | Sedaxane |
| 1-168 | Abamectin | Penflufen |
| 1-169 | Abamectin | Fluxapyroxad |
| 1-170 | Abamectin | *Bacillus firmus* |
| 1-171 | Abamectin | *Pasteuria penetrans* |
| 1-172 | Abamectin | Thiodicarb |
| 1-173 | Abamectin | Tolclophos-methyl |
| 1-174 | Abamectin | Ethaboxam |
| 1-175 | Abamectin | Compound 4 |
| 1-176 | Abamectin | Compound 2 |
| 1-177 | Abamectin | Compound 3 |
| 1-178 | Abamectin | Compound 1 |
| 1-179 | Abamectin | Compound 5 |
| 1-180 | Thiodicarb | Ipconazole |
| 1-181 | Thiodicarb | Metconazole |
| 1-182 | Thiodicarb | Diphenoconazole |
| 1-183 | Thiodicarb | Tebuconazole |
| 1-184 | Thiodicarb | Prothioconazole |
| 1-185 | Thiodicarb | Fluquinconazole |
| 1-186 | Thiodicarb | Triticonazole |
| 1-187 | Thiodicarb | Imazalil |
| 1-188 | Thiodicarb | Pencycuron |
| 1-189 | Thiodicarb | Prochloraz |
| 1-190 | Thiodicarb | Pyraclostrobin |
| 1-191 | Thiodicarb | Azoxystrobin |
| 1-192 | Thiodicarb | Trifloxystrobin |
| 1-193 | Thiodicarb | Metalaxyl |
| 1-194 | Thiodicarb | Metalaxyl-M |
| 1-195 | Thiodicarb | Fludioxonil |
| 1-196 | Thiodicarb | Thiram |
| 1-197 | Thiodicarb | Mancozeb |
| 1-198 | Thiodicarb | Flutolanil |
| 1-199 | Thiodicarb | Sedaxane |
| 1-200 | Thiodicarb | Penflufen |
| 1-201 | Thiodicarb | Fluxapyroxad |
| 1-202 | Thiodicarb | *Bacillus firmus* |
| 1-203 | Thiodicarb | *Pasteuria penetrans* |
| 1-204 | Thiodicarb | Tolclophos-methyl |
| 1-205 | Thiodicarb | Ethaboxam |
| 1-206 | Thiodicarb | Compound 4 |
| 1-207 | Thiodicarb | Compound 2 |
| 1-208 | Thiodicarb | Compound 3 |

TABLE 3-continued

| Number of combination | Combinations of compounds | |
|---|---|---|
| 1-209 | Thiodicarb | Compound 1 |
| 1-210 | Thiodicarb | Compound 5 |
| 1-211 | Thiodicarb | Furametpyr |
| 1-212 | Metalaxyl | Ipconazole |
| 1-213 | Metalaxyl | Metconazole |
| 1-214 | Metalaxyl | Diphenoconazole |
| 1-215 | Metalaxyl | Tebuconazole |
| 1-216 | Metalaxyl | Prothioconazole |
| 1-217 | Metalaxyl | Fluquinconazole |
| 1-218 | Metalaxyl | Triticonazole |
| 1-219 | Metalaxyl | Imazalil |
| 1-220 | Metalaxyl | Pencycuron |
| 1-221 | Metalaxyl | Prochloraz |
| 1-222 | Metalaxyl | Pyraclostrobin |
| 1-223 | Metalaxyl | Azoxystrobin |
| 1-224 | Metalaxyl | Trifloxystrobin |
| 1-225 | Metalaxyl | Fludioxonil |
| 1-226 | Metalaxyl | Thiram |
| 1-227 | Metalaxyl | Flutolanil |
| 1-228 | Metalaxyl | Sedaxane |
| 1-229 | Metalaxyl | Penflufen |
| 1-230 | Metalaxyl | Fluxapyroxad |
| 1-231 | Metalaxyl | *Bacillus firmus* |
| 1-232 | Metalaxyl | *Pasteuria penetrans* |
| 1-233 | Metalaxyl | Tolclophos-methyl |
| 1-234 | Metalaxyl | Ethaboxam |
| 1-235 | Metalaxyl | Compound 4 |
| 1-236 | Metalaxyl | Compound 2 |
| 1-237 | Metalaxyl | Compound 3 |
| 1-238 | Metalaxyl | Compound 1 |
| 1-239 | Metalaxyl | Compound 5 |
| 1-240 | Metalaxyl | Furametpyr |
| 1-241 | Metalaxyl-M | Ipconazole |
| 1-242 | Metalaxyl-M | Metconazole |
| 1-243 | Metalaxyl-M | Diphenoconazole |
| 1-244 | Metalaxyl-M | Tebuconazole |
| 1-245 | Metalaxyl-M | Prothioconazole |
| 1-246 | Metalaxyl-M | Fluquinconazole |
| 1-247 | Metalaxyl-M | Triticonazole |
| 1-248 | Metalaxyl-M | Imazalil |
| 1-249 | Metalaxyl-M | Pencycuron |
| 1-250 | Metalaxyl-M | Prochloraz |
| 1-251 | Metalaxyl-M | Pyraclostrobin |
| 1-252 | Metalaxyl-M | Azoxystrobin |
| 1-253 | Metalaxyl-M | Trifloxystrobin |
| 1-254 | Metalaxyl-M | Fludioxonil |
| 1-255 | Metalaxyl-M | Thiram |
| 1-256 | Metalaxyl-M | Flutolanil |
| 1-257 | Metalaxyl-M | Sedaxane |
| 1-258 | Metalaxyl-M | Penflufen |
| 1-259 | Metalaxyl-M | Fluxapyroxad |
| 1-260 | Metalaxyl-M | *Bacillus firmus* |
| 1-261 | Metalaxyl-M | *Pasteuria penetrans* |
| 1-262 | Metalaxyl-M | Tolclophos-methyl |
| 1-263 | Metalaxyl-M | Ethaboxam |
| 1-264 | Metalaxyl-M | Compound 4 |
| 1-265 | Metalaxyl-M | Compound 2 |
| 1-266 | Metalaxyl-M | Compound 3 |
| 1-267 | Metalaxyl-M | Compound 1 |
| 1-268 | Metalaxyl-M | Compound 5 |
| 1-269 | Metalaxyl-M | Furametpyr |
| 1-270 | Fludioxonil | Ipconazole |
| 1-271 | Fludioxonil | Metconazole |
| 1-272 | Fludioxonil | Diphenoconazole |
| 1-273 | Fludioxonil | Tebuconazole |
| 1-274 | Fludioxonil | Prothioconazole |
| 1-275 | Fludioxonil | Fluquinconazole |
| 1-276 | Fludioxonil | Triticonazole |
| 1-277 | Fludioxonil | Imazalil |
| 1-278 | Fludioxonil | Pencycuron |
| 1-279 | Fludioxonil | Prochloraz |
| 1-280 | Fludioxonil | Pyraclostrobin |
| 1-281 | Fludioxonil | Azoxystrobin |
| 1-282 | Fludioxonil | Trifloxystrobin |
| 1-283 | Fludioxonil | Thiram |
| 1-284 | Fludioxonil | Flutolanil |
| 1-285 | Fludioxonil | Sedaxane |

TABLE 3-continued

| Number of combination | Combinations of compounds | |
|---|---|---|
| 1-286 | Fludioxonil | Penflufen |
| 1-287 | Fludioxonil | Fluxapyroxad |
| 1-288 | Fludioxonil | *Bacillus firmus* |
| 1-289 | Fludioxonil | *Pasteuria penetrans* |
| 1-290 | Fludioxonil | Tolclophos-methyl |
| 1-291 | Fludioxonil | Ethaboxam |
| 1-292 | Fludioxonil | Compound 4 |
| 1-293 | Fludioxonil | Compound 2 |
| 1-294 | Fludioxonil | Compound 3 |
| 1-295 | Fludioxonil | Compound 1 |
| 1-296 | Fludioxonil | Compound 5 |
| 1-297 | Fludioxonil | Furametpyr |
| 1-298 | Ipconazole | Pyraclostrobin |
| 1-299 | Ipconazole | Azoxystrobin |
| 1-300 | Ipconazole | Trifloxystrobin |
| 1-301 | Ipconazole | Thiram |
| 1-302 | Ipconazole | Flutolanil |
| 1-303 | Ipconazole | Sedaxane |
| 1-304 | Ipconazole | Penflufen |
| 1-305 | Ipconazole | Fluxapyroxad |
| 1-306 | Ipconazole | *Bacillus firmus* |
| 1-307 | Ipconazole | *Pasteuria penetrans* |
| 1-308 | Ipconazole | Tolclophos-methyl |
| 1-309 | Ipconazole | Ethaboxam |
| 1-310 | Ipconazole | Compound 4 |
| 1-311 | Ipconazole | Compound 2 |
| 1-312 | Ipconazole | Compound 3 |
| 1-313 | Ipconazole | Compound 1 |
| 1-314 | Ipconazole | Compound 5 |
| 1-315 | Metconazole | Pyraclostrobin |
| 1-316 | Metconazole | Azoxystrobin |
| 1-317 | Metconazole | Trifloxystrobin |
| 1-318 | Metconazole | Thiram |
| 1-319 | Metconazole | Flutolanil |
| 1-320 | Metconazole | Sedaxane |
| 1-321 | Metconazole | Penflufen |
| 1-322 | Metconazole | Fluxapyroxad |
| 1-323 | Metconazole | *Bacillus firmus* |
| 1-324 | Metconazole | *Pasteuria penetrans* |
| 1-325 | Metconazole | Tolclophos-methyl |
| 1-326 | Metconazole | Ethaboxam |
| 1-327 | Metconazole | Compound 4 |
| 1-328 | Metconazole | Compound 2 |
| 1-329 | Metconazole | Compound 3 |
| 1-330 | Metconazole | Compound 1 |
| 1-331 | Metconazole | Compound 5 |
| 1-332 | Diphenoconazole | Pyraclostrobin |
| 1-333 | Diphenoconazole | Azoxystrobin |
| 1-334 | Diphenoconazole | Trifloxystrobin |
| 1-335 | Diphenoconazole | Thiram |
| 1-336 | Diphenoconazole | Flutolanil |
| 1-337 | Diphenoconazole | Sedaxane |
| 1-338 | Diphenoconazole | Penflufen |
| 1-339 | Diphenoconazole | Fluxapyroxad |
| 1-340 | Diphenoconazole | *Bacillus firmus* |
| 1-341 | Diphenoconazole | *Pasteuria penetrans* |
| 1-342 | Diphenoconazole | Tolclophos-methyl |
| 1-343 | Diphenoconazole | Ethaboxam |
| 1-344 | Diphenoconazole | Compound 4 |
| 1-345 | Diphenoconazole | Compound 2 |
| 1-346 | Diphenoconazole | Compound 3 |
| 1-347 | Diphenoconazole | Compound 1 |
| 1-348 | Diphenoconazole | Compound 5 |
| 1-349 | Prothioconazole | Pyraclostrobin |
| 1-350 | Prothioconazole | Azoxystrobin |
| 1-351 | Prothioconazole | Trifloxystrobin |
| 1-352 | Prothioconazole | Thiram |
| 1-353 | Prothioconazole | Flutolanil |
| 1-354 | Prothioconazole | Sedaxane |
| 1-355 | Prothioconazole | Penflufen |
| 1-356 | Prothioconazole | Fluxapyroxad |
| 1-357 | Prothioconazole | *Bacillus firmus* |
| 1-358 | Prothioconazole | *Pasteuria penetrans* |
| 1-359 | Prothioconazole | Tolclophos-methyl |
| 1-360 | Prothioconazole | Ethaboxam |
| 1-361 | Prothioconazole | Compound 4 |
| 1-362 | Prothioconazole | Compound 2 |

TABLE 3-continued

| Number of combination | Combinations of compounds | |
|---|---|---|
| 1-363 | Prothioconazole | Compound 3 |
| 1-364 | Prothioconazole | Compound 1 |
| 1-365 | Prothioconazole | Compound 5 |
| 1-366 | Fipronil | Tefluthrin |
| 1-367 | Imidacloprid | Tefluthrin |
| 1-368 | Carboxin | Thiram |
| 1-369 | Pyraclostrobin | Fluxapyroxad |
| 1-370 | Flutolanil | Mancozeb |
| 1-371 | Fluquinconazole | Prochloraz |

TABLE 4

| Number of combination | Combinations of compounds | |
|---|---|---|
| 2-1 | Combination of 1-14 | Pyraclostrobin |
| 2-2 | Combination of 1-14 | Azoxystrobin |
| 2-3 | Combination of 1-14 | Trifloxystrobin |
| 2-4 | Combination of 1-14 | Compound 1 |
| 2-5 | Combination of 1-14 | Metconazole |
| 2-6 | Combination of 1-14 | Prothioconazole |
| 2-7 | Combination of 1-14 | Triticonazole |
| 2-8 | Combination of 1-14 | Tebuconazole |
| 2-9 | Combination of 1-14 | Diphenoconazole |
| 2-10 | Combination of 1-14 | Ipconazole |
| 2-11 | Combination of 1-14 | Thiophanate-methyl |
| 2-12 | Combination of 1-14 | Fludioxonil |
| 2-13 | Combination of 1-14 | Tolclophos-methyl |
| 2-14 | Combination of 1-14 | Thiram |
| 2-15 | Combination of 1-14 | Captan |
| 2-16 | Combination of 1-14 | Carboxin |
| 2-17 | Combination of 1-14 | Boscalid |
| 2-18 | Combination of 1-14 | Thiabendazole |
| 2-19 | Combination of 1-14 | Ethaboxam |
| 2-20 | Combination of 1-15 | Pyraclostrobin |
| 2-21 | Combination of 1-15 | Azoxystrobin |
| 2-22 | Combination of 1-15 | Trifloxystrobin |
| 2-23 | Combination of 1-15 | Compound 1 |
| 2-24 | Combination of 1-15 | Metconazole |
| 2-25 | Combination of 1-15 | Prothioconazole |
| 2-26 | Combination of 1-15 | Triticonazole |
| 2-27 | Combination of 1-15 | Tebuconazole |
| 2-28 | Combination of 1-15 | Diphenoconazole |
| 2-29 | Combination of 1-15 | Ipconazole |
| 2-30 | Combination of 1-15 | Thiophanate-methyl |
| 2-31 | Combination of 1-15 | Fludioxonil |
| 2-32 | Combination of 1-15 | Tolclophos-methyl |
| 2-33 | Combination of 1-15 | Thiram |
| 2-34 | Combination of 1-15 | Captan |
| 2-35 | Combination of 1-15 | Carboxin |

TABLE 4-continued

| Number of combination | Combinations of compounds | |
|---|---|---|
| 2-36 | Combination of 1-15 | Boscalid |
| 2-37 | Combination of 1-15 | Thiabendazole |
| 2-38 | Combination of 1-15 | Ethaboxam |
| 2-39 | Combination of 1-18 | Pyraclostrobin |
| 2-40 | Combination of 1-18 | Azoxystrobin |
| 2-41 | Combination of 1-18 | Trifloxystrobin |
| 2-42 | Combination of 1-18 | Compound 1 |
| 2-43 | Combination of 1-18 | Metconazole |
| 2-44 | Combination of 1-18 | Prothioconazole |
| 2-45 | Combination of 1-18 | Triticonazole |
| 2-46 | Combination of 1-18 | Tebuconazole |
| 2-47 | Combination of 1-18 | Diphenoconazole |
| 2-48 | Combination of 1-18 | Ipconazole |
| 2-49 | Combination of 1-18 | Thiophanate-methyl |
| 2-50 | Combination of 1-18 | Fludioxonil |
| 2-51 | Combination of 1-18 | Tolclophos-methyl |
| 2-52 | Combination of 1-18 | Thiram |
| 2-53 | Combination of 1-18 | Captan |
| 2-54 | Combination of 1-18 | Carboxin |
| 2-55 | Combination of 1-18 | Boscalid |
| 2-56 | Combination of 1-18 | Thiabendazole |
| 2-57 | Combination of 1-28 | Boscalid |
| 2-58 | Combination of 1-28 | Metconazole |
| 2-59 | Combination of 1-28 | Ipconazole |
| 2-60 | Combination of 1-28 | Triticonazole |
| 2-61 | Combination of 1-28 | Tebuconazole |
| 2-62 | Combination of 1-28 | Thiabendazole |
| 2-63 | Combination of 1-28 | Carboxin |
| 2-64 | Combination of 1-28 | Penflufen |
| 2-65 | Combination of 1-28 | Sedaxane |
| 2-66 | Combination of 1-28 | Fluxapyroxad |
| 2-67 | Combination of 1-28 | Fluopyram |
| 2-68 | Combination of 1-28 | Thiram |
| 2-69 | Combination of 1-233 | Metconazole |
| 2-70 | Combination of 1-27 | Ipconazole |
| 2-71 | Combination of 1-14 | Compound 5 |
| 2-72 | Combination of 1-15 | Compound 5 |
| 2-73 | Combination of 1-28 | Compound 5 |
| 2-74 | Combination of 1-90 | Fludioxonil |
| 2-75 | Combination of 1-91 | Fludioxonil |
| 2-76 | Combination of 1-52 | Pyraclostrobin |
| 2-77 | Combination of 1-53 | Pyraclostrobin |
| 2-78 | Combination of 1-52 | Trifloxystrobin |
| 2-79 | Combination of 1-53 | Trifloxystrobin |
| 2-80 | Combination of 1-216 | Penflufen |
| 2-81 | Combination of 1-4 | *Bacillus firmus* |
| 2-82 | Combination of 1-52 | Tebuconazole |
| 2-83 | Combination of 1-53 | Tebuconazole |
| 2-84 | Combination of 1-42 | Triazoxide |
| 2-85 | Combination of 1-52 | Mycrobutanil |
| 2-86 | Combination of 1-53 | Mycrobutanil |

TABLE 5

| Number of combination | Combination of compounds | | |
|---|---|---|---|
| 3-1 | Combination of 2-57 | Pyraclostrobin | Compound 1 |
| 3-2 | Combination of 2-57 | Pyraclostrobin | Tolclophos-methyl |
| 3-3 | Combination of 2-57 | Pyraclostrobin | Metconazole |
| 3-4 | Combination of 2-57 | Pyraclostrobin | Metalaxyl |
| 3-5 | Combination of 2-17 | Pyraclostrobin | Metconazole |
| 3-6 | Combination of 2-36 | Pyraclostrobin | Metconazole |
| 3-7 | Combination of 2-17 | Pyraclostrobin | Compound 1 |
| 3-8 | Combination of 2-36 | Pyraclostrobin | Compound 1 |
| 3-9 | Combination of 2-17 | Pyraclostrobin | Tolclophos-methyl |
| 3-10 | Combination of 2-36 | Pyraclostrobin | Tolclophos-methyl |
| 3-11 | Combination of 2-10 | Thiram | |
| 3-12 | Combination of 2-14 | Trifloxystrobin | |
| 3-13 | Combination of 2-33 | Trifloxystrobin | |
| 3-14 | Combination of 2-24 | Trifloxystrobin | |
| 3-15 | Combination of 2-22 | Compound 1 | |
| 3-16 | Combination of 2-23 | Azoxystrobin | |
| 3-17 | Combination of 2-23 | Thiabendazole | |

TABLE 5-continued

| Number of combination | Combination of compounds | | |
|---|---|---|---|
| 3-18 | Combination of 2-32 | Trifloxystrobin | |
| 3-19 | Combination of 2-32 | Azoxystrobin | |
| 3-20 | Combination of 2-32 | Thiabendazole | |
| 3-21 | Combination of 2-19 | Trifloxystrobin | Compound 1 |
| 3-22 | Combination of 2-19 | Azoxystrobin | Compound 1 |
| 3-23 | Combination of 2-29 | Thiram | Compound 1 |
| 3-24 | Combination of 2-29 | Tolclophos-methyl | |
| 3-25 | Combination of 2-5 | Ethaboxam | Compound 1 |
| 3-26 | Combination of 2-58 | Compound 1 | |
| 3-27 | Combination of 2-58 | Diphenoconazole | |
| 3-28 | Combination of 2-5 | Diphenoconazole | |
| 3-29 | Combination of 2-24 | Diphenoconazole | |
| 3-30 | Combination of 2-59 | Diphenoconazole | |
| 3-31 | Combination of 2-60 | Diphenoconazole | |
| 3-32 | Combination of 2-61 | Diphenoconazole | |
| 3-33 | Combination of 2-62 | Diphenoconazole | |
| 3-34 | Combination of 2-63 | Diphenoconazole | |
| 3-35 | Combination of 2-64 | Diphenoconazole | |
| 3-36 | Combination of 2-65 | Diphenoconazole | |
| 3-37 | Combination of 2-66 | Diphenoconazole | |
| 3-38 | Combination of 2-67 | Diphenoconazole | |
| 3-39 | Combination of 2-68 | Diphenoconazole | |
| 3-40 | Combination of 2-19 | Metconazole | Diphenoconazole |
| 3-41 | Combination of 2-19 | Ipconazole | Diphenoconazole |
| 3-42 | Combination of 2-19 | Triticonazole | Diphenoconazole |
| 3-43 | Combination of 2-19 | Tebuconazole | Diphenoconazole |
| 3-44 | Combination of 2-19 | Thiabendazole | Diphenoconazole |
| 3-45 | Combination of 2-19 | Carboxin | Diphenoconazole |
| 3-46 | Combination of 2-19 | Penflufen | Diphenoconazole |
| 3-47 | Combination of 2-19 | Sedaxane | Diphenoconazole |
| 3-48 | Combination of 2-19 | Fluxapyroxad | Diphenoconazole |
| 3-49 | Combination of 2-19 | Fluopyram | Diphenoconazole |
| 3-50 | Combination of 2-19 | Thiram | Diphenoconazole |
| 3-51 | Combination of 2-17 | Pyraclostrobin | Ipconazole |
| 3-52 | Combination of 2-36 | Pyraclostrobin | Ipconazole |
| 3-53 | Combination of 2-57 | Pyraclostrobin | Ipconazole |
| 3-54 | Combination of 2-10 | Trifloxystrobin | |
| 3-55 | Combination of 2-29 | Trifloxystrobin | |
| 3-56 | Combination of 2-59 | Trifloxystrobin | |
| 3-57 | Combination of 2-19 | Ipconazole | Trifloxystrobin |
| 3-58 | Corchination of 2-29 | Azoxystrobin | |
| 3-59 | Combination of 2-59 | Azoxystrobin | |
| 3-60 | Combination of 2-19 | Ipconazole | Azoxystrobin |
| 3-61 | Combination of 2-5 | Compound 1 | Carboxin |
| 3-62 | Combination of 2-5 | Compound 1 | Penflufen |
| 3-63 | Combination of 2-5 | Compound 1 | Sedaxane |
| 3-64 | Combination of 2-5 | Compound 1 | Fluxapyroxad |
| 3-65 | Combination of 2-5 | Compound 1 | Fluopyram |
| 3-66 | Combination of 2-5 | Compound 1 | Oxycarboxin |
| 3-67 | Combination of 2-5 | Compound 1 | Thifluzamide |
| 3-68 | Combination of 2-5 | Compound 1 | Flutolanil |
| 3-69 | Combination of 2-5 | Compound 1 | Pencycuron |
| 3-70 | Combination of 2-5 | Compound 1 | Fludioxonil |
| 3-71 | Combination of 2-32 | Compound 1 | Metconazole |
| 3-72 | Combination of 2-32 | Compound 1 | Tebuconazole |
| 3-73 | Combination of 2-32 | Compound 1 | Diphenoconazole |
| 3-74 | Combination of 2-32 | Compound 1 | Triticonazole |
| 3-75 | Combination of 2-32 | Compound 1 | Imazalil |
| 3-76 | Combination of 2-32 | Compound 1 | Triadimenol |
| 3-77 | Combination of 2-32 | Compound 1 | Fluquinconazole |
| 3-78 | Combination of 2-32 | Compound 1 | Prochloraz |
| 3-79 | Combination of 2-32 | Compound 1 | Prothioconazole |
| 3-80 | Combination of 2-32 | Compound 1 | Diniconazole |
| 3-81 | Combination of 2-32 | Compound 1 | Diniconazole-M |
| 3-82 | Combination of 2-32 | Compound 1 | Ipconazole |
| 3-83 | Combination of 2-32 | Compound 1 | Cyproconazole |
| 3-84 | Combination of 2-32 | Compound 1 | Tetraconazole |
| 3-85 | Combination of 2-32 | Compound 1 | Carboxin |
| 3-86 | Combination of 2-32 | Compound 1 | Penflufen |
| 3-87 | Combination of 2-32 | Compound 1 | Sedaxane |
| 3-88 | Combination of 2-32 | Compound 1 | Fluxapyroxad |
| 3-89 | Combination of 2-32 | Compound 1 | Fluopyram |
| 3-90 | Combination of 2-32 | Compound 1 | Oxycarboxin |
| 3-91 | Combination of 2-32 | Compound 1 | Fludioxonil |
| 3-92 | Combination of 2-32 | Compound 1 | Thiram |
| 3-93 | Combination of 2-32 | Compound 1 | Captan |
| 3-94 | Combination of 2-32 | Compound 1 | Thiophanate-methyl |

TABLE 5-continued

| Number of combination | Combination of compounds | | | |
|---|---|---|---|---|
| 3-95 | Combination of 2-32 | Compound 1 | Thiabendazole | |
| 3-96 | Combination of 2-13 | Compound 1 | Metconazole | |
| 3-97 | Combination of 2-13 | Compound 1 | Tebuconazole | |
| 3-98 | Combination of 2-13 | Compound 1 | Diphenoconazole | |
| 3-99 | Combination of 2-13 | Compound 1 | Triticonazole | |
| 3-100 | Combination of 2-13 | Compound 1 | Imazalil | |
| 3-101 | Combination of 2-13 | Compound 1 | Triadimenol | |
| 3-102 | Combination of 2-13 | Compound 1 | Fluquinconazole | |
| 3-103 | Combination of 2-13 | Compound 1 | Prochloraz | |
| 3-104 | Combination of 2-13 | Compound 1 | Prothioconazole | |
| 3-105 | Combination of 2-13 | Compound 1 | Diniconazole | |
| 3-106 | Combination of 2-13 | Compound 1 | Diniconazole-M | |
| 3-107 | Combination of 2-13 | Compound 1 | Ipconazole | |
| 3-108 | Combination of 2-13 | Compound 1 | Cyproconazole | |
| 3-109 | Combination of 2-13 | Compound 1 | Tetraconazole | |
| 3-110 | Combination of 2-13 | Compound 1 | Carboxin | |
| 3-111 | Combination of 2-13 | Compound 1 | Penflufen | |
| 3-112 | Combination of 2-13 | Compound 1 | Sedaxane | |
| 3-113 | Combination of 2-13 | Compound 1 | Fluxapyroxad | |
| 3-114 | Combination of 2-13 | Compound 1 | Fluopyram | |
| 3-115 | Combination of 2-13 | Compound 1 | Oxycarboxin | |
| 3-116 | Combination of 2-13 | Compound 1 | Fludioxonil | |
| 3-117 | Combination of 2-13 | Compound 1 | Thiram | |
| 3-118 | Comhination of 2-13 | Compound 1 | Captan | |
| 3-119 | Combination of 2-13 | Compound 1 | Thiophanate-methyl | |
| 3-120 | Combination of 2-13 | Compound 1 | Thiabendazole | |
| 3-121 | Combination of 2-69 | Compound 1 | Oxadixyl | |
| 3-122 | Combination of 2-69 | Compound 1 | Hymexazol | |
| 3-123 | Combination of 2-69 | Compound 1 | Fenamidone | |
| 3-124 | Combination of 2-69 | Compound 1 | Cymoxanil | |
| 3-125 | Combination of 2-69 | Compound 1 | Fluopicolide | |
| 3-126 | Combination of 2-70 | Carboxin | | |
| 3-127 | Combination of 2-10 | Tolclophos-methyl | Carboxin | |
| 3-128 | Combination of 2-10 | Tolclophos-methyl | Penflufen | |
| 3-129 | Combination of 2-10 | Tolclophos-methyl | Sedaxane | |
| 3-130 | Combination of 2-10 | Tolclophos-methyl | Fluxapyroxad | |
| 3-131 | Combination of 2-10 | Tolclophos-methyl | Fluopyram | |
| 3-132 | Combination of 2-5 | Tolclophos-methyl | | |
| 3-133 | Combination of 2-5 | Tolclophos-methyl | Azoxystrobin | |
| 3-134 | Combination of 2-5 | Tolclophos-methyl | Fluoxastrobin | |
| 3-135 | Combination of 2-5 | Tolclophos-methyl | Trifloxystrobin | |
| 3-136 | Combination of 2-5 | Tolclophos-methyl | Pyraclostrobin | |
| 3-137 | Combination of 2-5 | Tolclophos-methyl | Orysastrobin | |
| 3-138 | Combination of 2-5 | Tolclophos-methyl | Carboxin | |
| 3-139 | Combination of 2-5 | Tolclophos-methyl | Oxycarboxin | |
| 3-140 | Combination of 2-5 | Tolclophos-methyl | Fludioxonil | |
| 3-141 | Combination of 2-5 | Tolclophos-methyl | Thiram | |
| 3-142 | Combination of 2-5 | Tolclophos-methyl | Captan | |
| 3-143 | Combination of 2-5 | Tolclophos-methyl | Thiophanate-methyl | |
| 3-144 | Combination of 2-5 | Tolclophos-methyl | Thiabendazole | |
| 3-145 | Combination of 2-5 | Ethaboxam | | |
| 3-146 | Combination of 2-5 | Ethaboxam | Tolclophos-methyl | |
| 3-147 | Combination of 2-38 | Compound 1 | Compound 2 | |
| 3-148 | Combination of 2-19 | Compound 1 | Compound 2 | |
| 3-149 | Combination of 2-19 | Compound 5 | Compound 2 | |
| 3-150 | Combination of 2-38 | Compound 5 | Compound 2 | |
| 3-151 | Combination of 2-19 | Ipconazole | Compound 3 | |
| 3-152 | Combination of 2-38 | Ipconazole | Compound 3 | |
| 3-153 | Combination of 2-19 | Metconazole | Compound 3 | |
| 3-154 | Combination of 2-38 | Metconazole | Compound 3 | |
| 3-155 | Combination of 2-19 | Tolclophos-methyl | Compound 3 | |
| 3-156 | Combination of 2-38 | Tolclophos-methyl | Compound 3 | |
| 3-157 | Combination of 2-19 | Compound 1 | Compound 3 | |
| 3-158 | Combination of 2-38 | Compound 1 | Compound 3 | |
| 3-159 | Combination of 2-19 | Compound 1 | Compound 3 | |
| 3-160 | Combination of 2-38 | Compound 1 | Compound 3 | |
| 3-161 | Combination of 2-19 | Compound 5 | Compound 3 | |
| 3-162 | Combination of 2-38 | Fludioxonil | Compound 3 | |
| 3-163 | Combination of 2-38 | Compound 5 | Compound 3 | |
| 3-164 | Combination of 2-19 | Tolclophos-methyl | Compound 4 | |
| 3-165 | Combination of 2-38 | Metconazole | Compound 4 | |
| 3-166 | Combination of 2-38 | Compound 4 | Compound 5 | |
| 3-167 | Combination of 2-38 | Compound 4 | Compound 1 | |
| 3-168 | Combination of 2-19 | Ipconazole | Compound 4 | |
| 3-169 | Combination of 2-19 | Compound 4 | Compound 5 | |
| 3-170 | Combination of 2-19 | Boscalid | Pyraclostrobin | Metconazole |
| 3-171 | Combination of 2-19 | Boscalid | Pyraclostrobin | Ipconazole |

TABLE 5-continued

| Number of combination | Combination of compounds | | | |
|---|---|---|---|---|
| 3-172 | Combination of 2-38 | Boscalid | Pyraclostrobin | Metconazole |
| 3-173 | Combination of 2-19 | Boscalid | Pyraclostrobin | Compound 1 |
| 3-174 | Combination of 2-38 | Boscalid | Pyraclostrobin | Compound 1 |
| 3-175 | Combination of 2-19 | Boscalid | Pyraclostrobin | Tolclophos-methyl |
| 3-176 | Combination of 2-38 | Boscalid | Pyraclostrobin | Tolclophos-methyl |
| 3-177 | Corchination of 2-32 | Compound 1 | Metconazole | Oxadixyl |
| 3-178 | Combination of 2-32 | Compound 1 | Metconazole | Hymexazol |
| 3-179 | Combination of 2-32 | Compound 1 | Metconazole | Fenamidone |
| 3-180 | Combination of 2-32 | Compound 1 | Metconazole | Cymoxanil |
| 3-181 | Combination of 2-32 | Compound 1 | Metconazole | Fluopicolide |
| 3-182 | Combination of 2-13 | Compound 1 | Metconazole | Oxadixyl |
| 3-183 | Combination of 2-13 | Compound 1 | Metconazole | Hymexazol |
| 3-184 | Combination of 2-13 | Compound 1 | Metconazole | Fenamidone |
| 3-185 | Combination of 2-13 | Compound 1 | Metconazole | Cymoxanil |
| 3-186 | Combination of 2-13 | Compound 1 | Metconazole | Fluopicolide |
| 3-187 | Combination of 2-5 | Ethaboxam | Tolclophos-methyl | Azoxystrobin |
| 3-188 | Combination of 2-5 | Ethaboxam | Tolclophos-methyl | Fluoxastrobin |
| 3-189 | Combination of 2-5 | Ethaboxam | Tolclophos-methyl | Trifloxystrobin |
| 3-190 | Combination of 2-5 | Ethaboxam | Tolclophos-methyl | Pyraclostrobin |
| 3-191 | Combination of 2-5 | Ethaboxam | Tolclophos-methyl | Orysastrobin |
| 3-192 | Combination of 2-5 | Ethaboxam | Tolclophos-methyl | Carboxin |
| 3-193 | Combination of 2-5 | Ethaboxam | Tolclophos-methyl | Penflufen |
| 3-194 | Combination of 2-5 | Ethaboxam | Tolclophos-methyl | Sedaxane |
| 3-195 | Combination of 2-5 | Ethaboxam | Tolclophos-methyl | Fluxapyroxad |
| 3-196 | Combination of 2-19 | Ipconazole | Compound 2 | Fluopyram |
| 3-197 | Combination of 2-38 | Ipconazole | Compound 2 | Oxycarboxin |
| 3-198 | Combination of 2-19 | Metconazole | Compound 2 | Fludioxonil |
| 3-199 | Combination of 2-38 | Metconazole | Compound 2 | Thiram |
| 3-200 | Combination of 2-19 | Tolclophos-methyl | Compound 2 | Captan |
| 3-201 | Combination of 2-38 | Tolclophos-methyl | Compound 2 | Thiophanate-methyl |
| 3-202 | Combination of 2-19 | Compound 1 | Compound 2 | Thiabendazole |
| 3-203 | Combination of 2-72 | Metconazole | | |
| 3-204 | Combination of 2-71 | Metconazole | | |
| 3-205 | Combination of 2-73 | Diphenoconazole | | |
| 3-206 | Combination of 2-73 | Triticonazole | | |
| 3-207 | Combination of 2-73 | Tebuconazole | | |
| 3-208 | Combination of 2-73 | Thiabendazole | | |
| 3-209 | Combination of 2-73 | Carboxin | | |
| 3-210 | Combination of 2-73 | Thiram | | |
| 3-211 | Combination of 2-73 | Captan | | |
| 3-212 | Combination of 2-71 | Compound 1 | | |
| 3-213 | Combination of 2-72 | Compound 1 | | |
| 3-214 | Combination of 2-73 | Compound 1 | | |
| 3-215 | Combination of 2-71 | Tolclophos-methyl | | |
| 3-216 | Combination of 2-72 | Tolclophos-methyl | | |
| 3-217 | Combination of 2-71 | Captan | | |
| 3-218 | Combination of 2-72 | Captan | | |
| 3-219 | Combination of 2-71 | Ethaboxam | Metconazole | |
| 3-220 | Combination of 2-71 | Ethaboxam | Compound 1 | |
| 3-221 | Combination of 2-71 | Ethaboxam | Tolclophos-methyl | |
| 3-222 | Combination of 2-73 | Tolclophos-methyl | | |
| 3-223 | Combination of 2-71 | Ethaboxam | Ipconazole | |
| 3-224 | Combination of 2-71 | Ethaboxam | Diphenoconazole | |
| 3-225 | Combination of 2-71 | Ethaboxam | Triticonazole | |
| 3-226 | Combination of 2-71 | Ethaboxam | Tebuconazole | |
| 3-227 | Combination of 2-71 | Ethaboxam | Thiabendazole | |
| 3-228 | Combination of 2-71 | Ethaboxam | Carboxin | |
| 3-229 | Combination of 2-71 | Ethaboxam | Thiram | |
| 3-230 | Combination of 2-71 | Ethaboxam | Captan | |
| 3-231 | Combination of 2-73 | Ipconazole | | |
| 3-232 | Combination of 2-71 | Fludioxonil | Azoxystrobin | Prothioconazole |
| 3-233 | Combination of 2-71 | Fludioxonil | Pyraclostrobin | Prothioconazole |
| 3-234 | Combination of 2-71 | Fludioxonil | Trifloxystrobin | Prothioconazole |
| 3-235 | Combination of 2-71 | Fludioxonil | Fluoxastrobin | Prothioconazole |
| 3-236 | Combination of 2-71 | Fludioxonil | Azoxystrobin | Triticonazole |
| 3-237 | Corchination of 2-71 | Fludioxonil | Pyraclostrobin | Triticonazole |
| 3-238 | Combination of 2-71 | Fludioxonil | Trifloxystrobin | Triticonazole |
| 3-239 | Combination of 2-71 | Fludioxonil | Fluoxastrobin | Triticonazole |
| 3-240 | Combination of 2-71 | Fludioxonil | Azoxystrobin | Tebuconazole |
| 3-241 | Combination of 2-71 | Fludioxonil | Pyraclostrobin | Tebuconazole |
| 3-242 | Combination of 2-71 | Fludioxonil | Trifloxystrobin | Tebuconazole |
| 3-243 | Combination of 2-71 | Fludioxonil | Fluoxastrobin | Tebuconazole |
| 3-244 | Combination of 2-71 | Fludioxonil | Azoxystrobin | Diphenoconazole |
| 3-245 | Combination of 2-71 | Fludioxonil | Pyraclostrobin | Diphenoconazole |
| 3-246 | Combination of 2-71 | Fludioxonil | Trifloxystrobin | Diphenoconazole |
| 3-247 | Combination of 2-71 | Fludioxonil | Fluoxastrobin | Diphenoconazole |
| 3-248 | Combination of 2-72 | Fludioxonil | Azoxystrobin | Prothioconazole |

TABLE 5-continued

| Number of combination | Combination of compounds | | | |
|---|---|---|---|---|
| 3-249 | Combination of 2-72 | Fludioxonil | Pyraclostrobin | Prothioconazole |
| 3-250 | Combination of 2-72 | Fludioxonil | Trifloxystrobin | Prothioconazole |
| 3-251 | Combination of 2-72 | Fludioxonil | Fluoxastrobin | Prothioconazole |
| 3-252 | Combination of 2-72 | Fludioxonil | Azoxystrobin | Triticonazole |
| 3-253 | Combination of 2-72 | Fludioxonil | Pyraclostrobin | Triticonazole |
| 3-254 | Combination of 2-72 | Fludioxonil | Trifloxystrobin | Triticonazole |
| 3-255 | Combination of 2-72 | Fludioxonil | Fluoxastrobin | Triticonazole |
| 3-256 | Combination of 2-72 | Fludioxonil | Azoxystrobin | Tebuconazole |
| 3-257 | Combination of 2-72 | Fludioxonil | Pyraclostrobin | Tebuconazole |
| 3-258 | Combination of 2-72 | Fludioxonil | Trifloxystrobin | Tebuconazole |
| 3-259 | Combination of 2-72 | Fludioxonil | Fluoxastrobin | Tebuconazole |
| 3-260 | Combination of 2-72 | Fludioxonil | Azoxystrobin | Diphenoconazole |
| 3-261 | Combination of 2-72 | Fludioxonil | Pyraclostrobin | Diphenoconazole |
| 3-262 | Combination of 2-72 | Fludioxonil | Trifloxystrobin | Diphenoconazole |
| 3-263 | Combination of 2-72 | Fludioxonil | Fluoxastrobin | Diphenoconazole |
| 3-264 | Combination of 2-71 | Compound 1 | Compound 2 | |
| 3-265 | Combination of 2-71 | Pyraclostrobin | Compound 2 | |
| 3-266 | Combination of 2-71 | Azoxystrobin | Compound 2 | |
| 3-267 | Combination of 2-71 | Trifloxystrobin | Compound 2 | |
| 3-268 | Combination of 2-71 | Metconazole | Compound 2 | |
| 3-269 | Combination of 2-71 | Prothioconazole | Compound 2 | |
| 3-270 | Combination of 2-71 | Triticonazole | Compound 2 | |
| 3-271 | Combination of 2-71 | Tebuconazole | Compound 2 | |
| 3-272 | Combination of 2-71 | Diphenoconazole | Compound 2 | |
| 3-273 | Combination of 2-71 | Ipconazole | Compound 2 | |
| 3-274 | Combination of 2-71 | Thiophanate-methyl | Compound 2 | |
| 3-275 | Combination of 2-71 | Fludioxonil | Compound 2 | |
| 3-276 | Combination of 2-71 | Tolclophos-methyl | Compound 2 | |
| 3-277 | Combination of 2-71 | Thiuram | Compound 2 | |
| 3-278 | Combination of 2-71 | Captan | Compound 2 | |
| 3-279 | Combination of 2-71 | Carboxin | Compound 2 | |
| 3-280 | Combination of 2-71 | Penflufen | Compound 2 | |
| 3-281 | Combination of 2-71 | Sedaxane | Compound 2 | |
| 3-282 | Combination of 2-71 | Fluxapyroxad | Compound 2 | |
| 3-283 | Combination of 2-71 | Fluopyram | Compound 2 | |
| 3-284 | Combination of 2-71 | Boscalid | Compound 2 | |
| 3-285 | Combination of 2-71 | Thiabendazole | Compound 2 | |
| 3-286 | Combination of 2-72 | Compound 1 | Compound 2 | |
| 3-287 | Combination of 2-72 | Pyraclostrobin | Compound 2 | |
| 3-288 | Combination of 2-72 | Azoxystrobin | Compound 2 | |
| 3-289 | Combination of 2-72 | Trifloxystrobin | Compound 2 | |
| 3-290 | Combination of 2-72 | Metconazole | Compound 2 | |
| 3-291 | Combination of 2-72 | Prothioconazole | Compound 2 | |
| 3-292 | Combination of 2-72 | Triticonazole | Compound 2 | |
| 3-293 | Combination of 2-72 | Tebuconazole | Compound 2 | |
| 3-294 | Combination of 2-72 | Diphenoconazole | Compound 2 | |
| 3-295 | Combination of 2-72 | Ipconazole | Compound 2 | |
| 3-296 | Combination of 2-72 | Thiophanate-methyl | Compound 2 | |
| 3-297 | Combination of 2-72 | Fludioxonil | Compound 2 | |
| 3-298 | Corchination of 2-72 | Tolclophos-methyl | Compound 2 | |
| 3-299 | Combination of 2-72 | Thiuram | Compound 2 | |
| 3-300 | Combination of 2-72 | Captan | Compound 2 | |
| 3-301 | Combination of 2-72 | Carboxin | Compound 2 | |
| 3-302 | Combination of 2-72 | Penflufen | Compound 2 | |
| 3-303 | Combination of 2-72 | Sedaxane | Compound 2 | |
| 3-304 | Combination of 2-72 | Fluxapyroxad | Compound 2 | |
| 3-305 | Combination of 2-72 | Fluopyram | Compound 2 | |
| 3-306 | Combination of 2-72 | Boscalid | Compound 2 | |
| 3-307 | Combination of 2-72 | Thiabendazole | Compound 2 | |
| 3-308 | Combination of 2-71 | Compound 1 | Compound 3 | |
| 3-309 | Combination of 2-71 | Pyraclostrobin | Compound 3 | |
| 3-310 | Combination of 2-71 | Azoxystrobin | Compound 3 | |
| 3-311 | Combination of 2-71 | Trifloxystrobin | Compound 3 | |
| 3-312 | Combination of 2-71 | Metconazole | Compound 3 | |
| 3-313 | Combination of 2-71 | Prothioconazole | Compound 3 | |
| 3-314 | Combination of 2-71 | Triticonazole | Compound 3 | |
| 3-315 | Combination of 2-71 | Tebuconazole | Compound 3 | |
| 3-316 | Combination of 2-71 | Diphenoconazole | Compound 3 | |
| 3-317 | Combination of 2-71 | Ipconazole | Compound 3 | |
| 3-318 | Combination of 2-71 | Thiophanate-methyl | Compound 3 | |
| 3-319 | Combination of 2-71 | Fludioxonil | Compound 3 | |
| 3-320 | Combination of 2-71 | Tolclophos-methyl | Compound 3 | |
| 3-321 | Combination of 2-71 | Thiuram | Compound 3 | |
| 3-322 | Combination of 2-71 | Captan | Compound 3 | |
| 3-323 | Combination of 2-71 | Carboxin | Compound 3 | |
| 3-324 | Combination of 2-71 | Penflufen | Compound 3 | |
| 3-325 | Combination of 2-71 | Sedaxane | Compound 3 | |

TABLE 5-continued

| Number of combination | Combination of compounds | | | |
|---|---|---|---|---|
| 3-326 | Combination of 2-71 | Fluxapyroxad | Compound 3 | |
| 3-327 | Combination of 2-71 | Fluopyram | Compound 3 | |
| 3-328 | Combination of 2-71 | Boscalid | Compound 3 | |
| 3-329 | Combination of 2-71 | Thiabendazole | Compound 3 | |
| 3-330 | Combination of 2-72 | Compound 1 | Compound 3 | |
| 3-331 | Combination of 2-72 | Pyraclostrobin | Compound 3 | |
| 3-332 | Combination of 2-72 | Azoxystrobin | Compound 3 | |
| 3-333 | Combination of 2-72 | Trifloxystrobin | Compound 3 | |
| 3-334 | Combination of 2-72 | Metconazole | Compound 3 | |
| 3-335 | Combination of 2-72 | Prothioconazole | Compound 3 | |
| 3-336 | Combination of 2-72 | Triticonazole | Compound 3 | |
| 3-337 | Combination of 2-72 | Tebuconazole | Compound 3 | |
| 3-338 | Combination of 2-72 | Diphenoconazole | Compound 3 | |
| 3-339 | Combination of 2-72 | Ipconazole | Compound 3 | |
| 3-340 | Combination of 2-72 | Thiophanate-methyl | Compound 3 | |
| 3-341 | Combination of 2-72 | Fludioxonil | Compound 3 | |
| 3-342 | Combination of 2-72 | Tolclophos-methyl | Compound 3 | |
| 3-343 | Combination of 2-72 | Thiuram | Compound 3 | |
| 3-344 | Combination of 2-72 | Captan | Compound 3 | |
| 3-345 | Combination of 2-72 | Carboxin | Compound 3 | |
| 3-346 | Combination of 2-72 | Penflufen | Compound 3 | |
| 3-347 | Combination of 2-72 | Sedaxane | Compound 3 | |
| 3-348 | Combination of 2-72 | Fluxapyroxad | Compound 3 | |
| 3-349 | Combination of 2-72 | Fluopyram | Compound 3 | |
| 3-350 | Combination of 2-72 | Boscalid | Compound 3 | |
| 3-351 | Combination of 2-72 | Thiabendazole | Compound 3 | |
| 3-352 | Combination of 2-71 | Compound 1 | Compound 4 | |
| 3-353 | Combination of 2-71 | Pyraclostrobin | Compound 4 | |
| 3-354 | Combination of 2-71 | Azoxystrobin | Compound 4 | |
| 3-355 | Combination of 2-71 | Trifloxystrobin | Compound 4 | |
| 3-356 | Combination of 2-71 | Metconazole | Compound 4 | |
| 3-357 | Combination of 2-71 | Prothioconazole | Compound 4 | |
| 3-358 | Combination of 2-71 | Triticonazole | Compound 4 | |
| 3-359 | Corchination of 2-71 | Tebuconazole | Compound 4 | |
| 3-360 | Combination of 2-71 | Diphenoconazole | Compound 4 | |
| 3-361 | Combination of 2-71 | Ipconazole | Compound 4 | |
| 3-362 | Combination of 2-71 | Thiophanate-methyl | Compound 4 | |
| 3-363 | Combination of 2-71 | Fludioxonil | Compound 4 | |
| 3-364 | Combination of 2-71 | Tolclophos-methyl | Compound 4 | |
| 3-365 | Combination of 2-71 | Thiuram | Compound 4 | |
| 3-366 | Combination of 2-71 | Captan | Compound 4 | |
| 3-367 | Combination of 2-71 | Carboxin | Compound 4 | |
| 3-368 | Combination of 2-71 | Penflufen | Compound 4 | |
| 3-369 | Combination of 2-71 | Sedaxane | Compound 4 | |
| 3-370 | Combination of 2-71 | Fluxapyroxad | Compound 4 | |
| 3-371 | Combination of 2-71 | Fluopyram | Compound 4 | |
| 3-372 | Combination of 2-71 | Boscalid | Compound 4 | |
| 3-373 | Combination of 2-71 | Thiabendazole | Compound 4 | |
| 3-374 | Combination of 2-72 | Compound 1 | Compound 4 | |
| 3-375 | Combination of 2-72 | Pyraclostrobin | Compound 4 | |
| 3-376 | Combination of 2-72 | Azoxystrobin | Compound 4 | |
| 3-377 | Combination of 2-72 | Trifloxystrobin | Compound 4 | |
| 3-378 | Combination of 2-72 | Metconazole | Compound 4 | |
| 3-379 | Combination of 2-72 | Prothioconazole | Compound 4 | |
| 3-380 | Combination of 2-72 | Triticonazole | Compound 4 | |
| 3-381 | Combination of 2-72 | Tebuconazole | Compound 4 | |
| 3-382 | Combination of 2-72 | Diphenoconazole | Compound 4 | |
| 3-383 | Combination of 2-72 | Ipconazole | Compound 4 | |
| 3-384 | Combination of 2-72 | Thiophanate-methyl | Compound 4 | |
| 3-385 | Combination of 2-72 | Fludioxonil | Compound 4 | |
| 3-386 | Combination of 2-72 | Tolclophos-methyl | Compound 4 | |
| 3-387 | Combination of 2-72 | Thiuram | Compound 4 | |
| 3-388 | Combination of 2-72 | Captan | Compound 4 | |
| 3-389 | Combination of 2-72 | Carboxin | Compound 4 | |
| 3-390 | Combination of 2-72 | Penflufen | Compound 4 | |
| 3-391 | Combination of 2-72 | Sedaxane | Compound 4 | |
| 3-392 | Combination of 2-72 | Fluxapyroxad | Compound 4 | |
| 3-393 | Combination of 2-72 | Fluopyram | Compound 4 | |
| 3-394 | Combination of 2-72 | Boscalid | Compound 4 | |
| 3-395 | Combination of 2-72 | Thiabendazole | Compound 4 | |
| 3-396 | Combination of 2-74 | Azoxystrobin | Abamectin | Sedaxane |
| 3-397 | Combination of 2-75 | Azoxystrobin | Abamectin | Sedaxane |
| 3-398 | Combination of 2-76 | Fluxapyroxad | | |
| 3-399 | Combination of 2-77 | Fluxapyroxad | | |
| 3-400 | Combination of 2-81 | Fluxapyroxad | | |
| 3-401 | Combination of 2-78 | Penflufen | | |
| 3-402 | Combination of 2-79 | Penflufen | | |

TABLE 5-continued

| Number of combination | Combination of compounds | | | |
|---|---|---|---|---|
| 3-403 | Fipronil | Pyraclostrobin | Thiophanate-methyl | Fluxapyroxad |
| 3-404 | Fluoxastrobin | Prothioconazole | Tebuconazole | Triazoxide |
| 3-405 | Combination of 3-398 | Sedaxane | | |
| 3-406 | Combination of 3-399 | Sedaxane | | |
| 3-407 | Combination of 2-85 | Trifloxystrobin | Fluxapyroxad | Thiodicarb |
| 3-408 | Combination of 2-86 | Trifloxystrobin | Fluxapyroxad | Thiodicarb |
| 3-409 | Combination of 2-85 | Pyraclostrobin | Fluxapyroxad | Thiodicarb |
| 3-410 | Combination of 2-86 | Pyraclostrobin | Fluxapyroxad | Thiodicarb |

According to the method of controlling pests of the present invention, pests in clop fields can be efficiently controlled.

What is claimed is:

1. A method of controlling plant pathogens in a crop field, the method including the steps of:

treating crop seeds or vegetative organs with clothianidin; and treating the crop field with crystal of flumioxazin, before sowing or planting, at the same time of sowing or planting, or after sowing or planting the crop seeds or vegetative organs which are treated with clothianidin, wherein the crystal of flumioxazin shows a powder X-Ray diffraction pattern having diffraction peaks with 2θ values (°) shown in Table, said pattern being obtained by CuKα rays diffraction analysis, Table

| 2θ value (°) |
|---|
| 9.8 ± 0.1 |
| 11.4 ± 0.1 |
| 12.7 ± 0.1 |
| 13.8 ± 0.1 |
| 16.0 ± 0.1 |
| 16.4 ± 0.1 |
| 16.7 ± 0.1. |

2. The control method according to claim 1, wherein the crop is soybean, peanut, common bean, pea, corn, cotton, wheat, rice, sunflower, potato, sugar cane, or vegetables.

* * * * *